(12) United States Patent
Epstein et al.

(10) Patent No.: US 9,861,426 B2
(45) Date of Patent: *Jan. 9, 2018

(54) ANCHORED RF ABLATION DEVICE FOR THE DESTRUCTION OF TISSUE MASSES

(71) Applicant: Acessa Health Inc., Austin, TX (US)

(72) Inventors: Gordon Epstein, Austin, TX (US); Bruce Lee, Austin, TX (US); Jeffrey M. Cohen, Austin, TX (US); Adam Hagmann, Austin, TX (US); Richard Spero, Austin, TX (US)

(73) Assignee: Acessa Health Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/969,600

(22) Filed: Aug. 18, 2013

(65) Prior Publication Data

US 2015/0066003 A1 Mar. 5, 2015
US 2017/0296256 A9 Oct. 19, 2017

Related U.S. Application Data

(63) Continuation of application No. 11/429,921, filed on May 8, 2006, now Pat. No. 8,512,333, which is a
(Continued)

(51) Int. Cl.
*A61B 18/14* (2006.01)
*A61B 18/18* (2006.01)
(Continued)

(52) U.S. Cl.
CPC .......... *A61B 18/14* (2013.01); *A61B 17/3421* (2013.01); *A61B 18/1477* (2013.01);
(Continued)

(58) Field of Classification Search
CPC .. A61B 2018/00559; A61B 2018/1405; A61B 2018/1467; A61B 2018/143;
(Continued)

(56) References Cited

U.S. PATENT DOCUMENTS 5,370,675 A * 12/1994 Edwards et al. .............. 607/101
5,454,782 A * 10/1995 Perkins .................. A61B 18/24
604/20

(Continued)

FOREIGN PATENT DOCUMENTS

DE 2124684 * 11/1972

*Primary Examiner* — Michael Peffley
(74) *Attorney, Agent, or Firm* — Levine Bagade Han LLP

(57) ABSTRACT

The inventive ablation element comprises an elongated cannula having a proximal end and a distal end. The cannula defines an internal lumen and a cannula axis. A plurality of conductors contained within the lumen, each having a proximal end proximate the proximal end of the cannula, and a distal end proximate the distal end of the cannula. A plurality of ablation stylets each has a proximal end and a distal end, and each coupled to the distal end of a respective conductor, the conductors together with their respective stylets being mounted for axial movement. A trocar point defined proximate the distal end of the cannula. A deflection surface positioned between the trocar point and the proximal end of the cannula, the deflection surface being configured and positioned to deflect at least some of the stylets laterally with respect to the cannula axis in different directions defining an ablation volume.

39 Claims, 20 Drawing Sheets

Related U.S. Application Data continuation-in-part of application No. 11/173,928, filed on Jul. 1, 2005, now Pat. No. 8,080,009.

(51) Int. Cl.
 *A61B 17/34* (2006.01)
 *A61B 18/00* (2006.01)

(52) U.S. Cl.
 CPC .......... *A61B 18/18* (2013.01); *A61B 18/1815* (2013.01); *A61B 2017/3454* (2013.01); *A61B 2018/0094* (2013.01); *A61B 2018/00214* (2013.01); *A61B 2018/00273* (2013.01); *A61B 2018/00559* (2013.01); *A61B 2018/00577* (2013.01); *A61B 2018/00702* (2013.01); *A61B 2018/00738* (2013.01); *A61B 2018/00761* (2013.01); *A61B 2018/00791* (2013.01); *A61B 2018/143* (2013.01); *A61B 2018/1405* (2013.01); *A61B 2018/1425* (2013.01); *A61B 2018/1432* (2013.01); *A61B 2018/1467* (2013.01); *A61B 2018/1475* (2013.01); *A61B 2018/1869* (2013.01)

(58) Field of Classification Search
 CPC .. A61B 2018/00791; A61B 2018/1475; A61B 2018/00577; A61B 2018/1432; A61B 18/14; A61B 18/1477; A61B 18/1815
 See application file for complete search history.

(56) References Cited

U.S. PATENT DOCUMENTS

| | | | | |
|---|---|---|---|---|
| 5,683,384 A | * | 11/1997 | Gough et al. | 606/41 |
| 5,810,804 A | * | 9/1998 | Gough et al. | 606/41 |
| 5,827,276 A | * | 10/1998 | LeVeen et al. | 606/41 |
| 5,849,011 A | * | 12/1998 | Jones | A61B 18/1477 606/41 |
| 6,016,452 A | * | 1/2000 | Kasevich | A61B 18/1206 606/41 |
| 6,221,071 B1 | * | 4/2001 | Sherry et al. | 606/41 |
| 6,974,455 B2 | * | 12/2005 | Garabedian et al. | 606/41 |

* cited by examiner

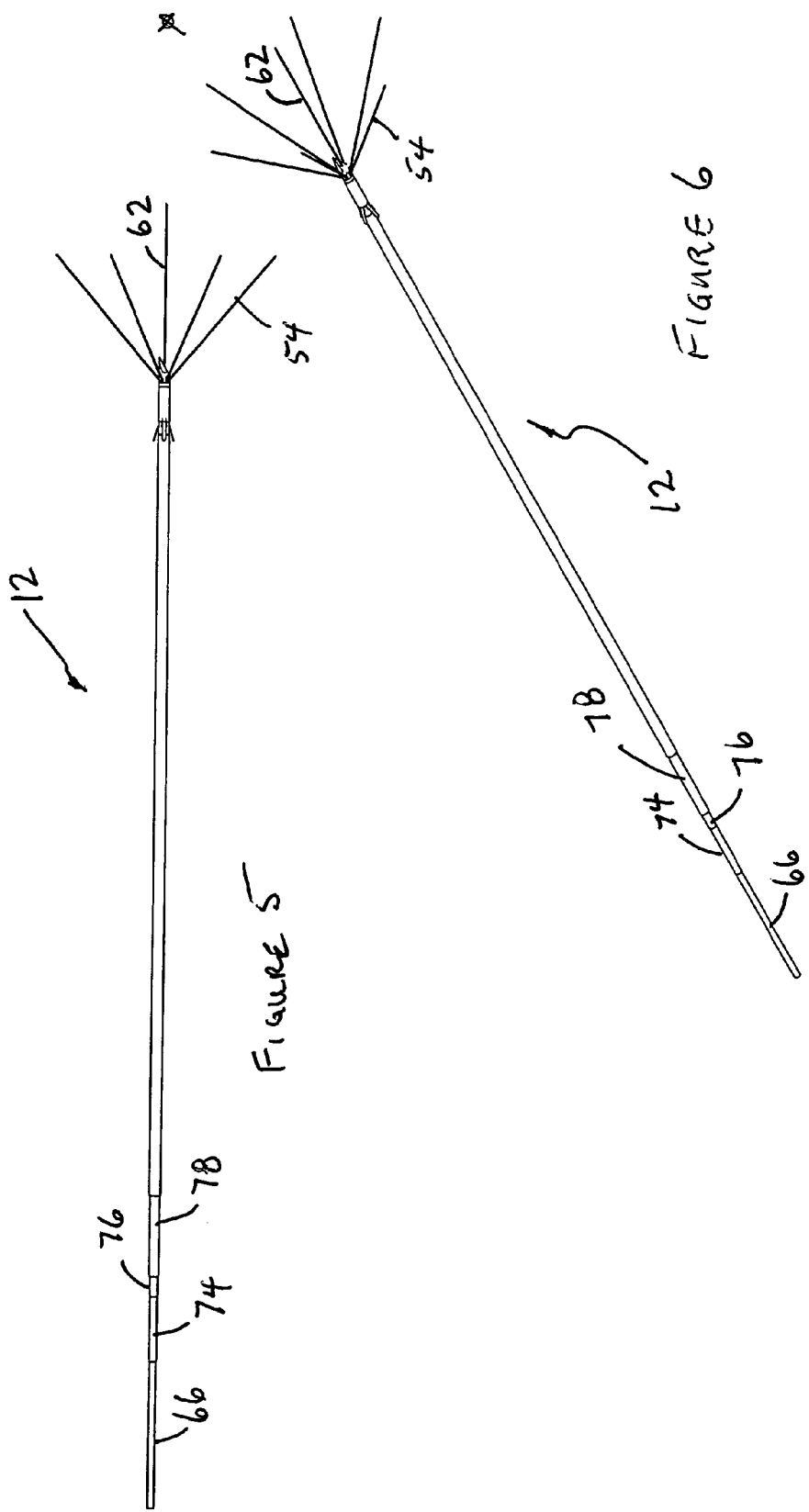

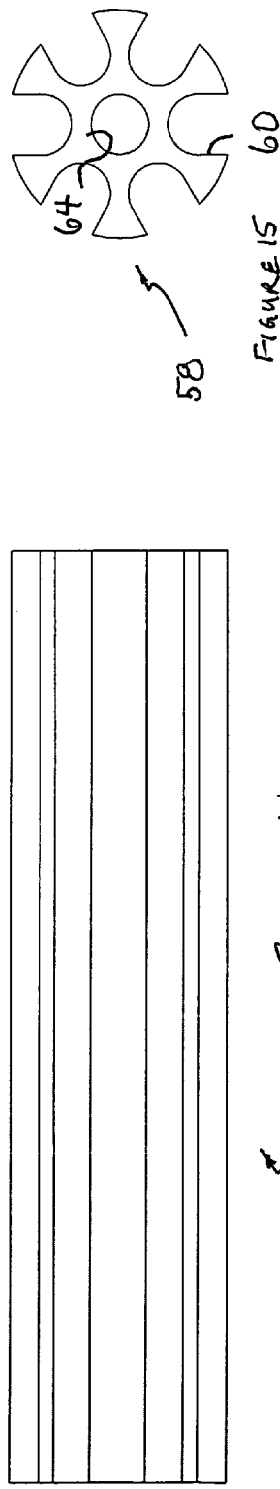
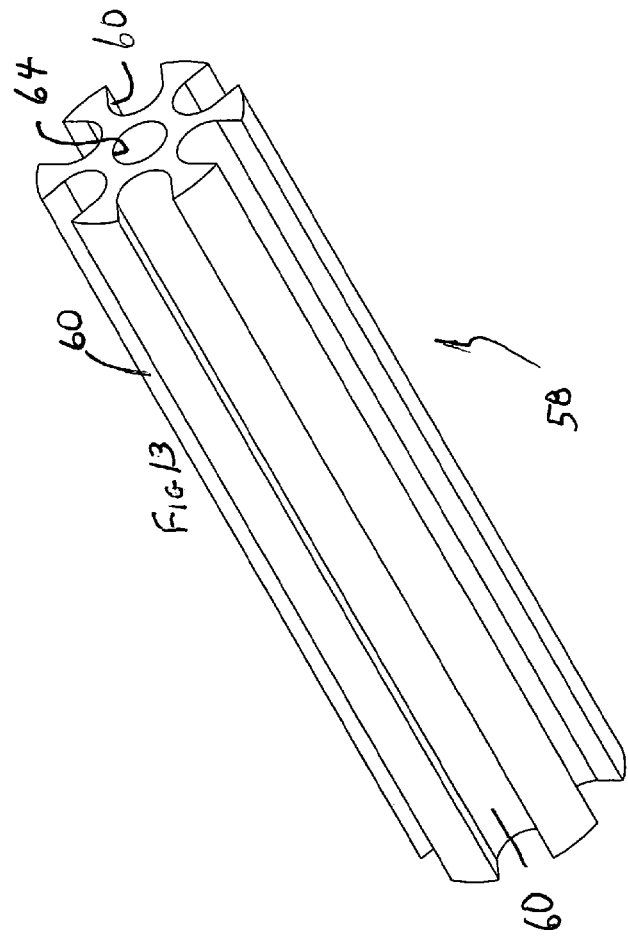
FIGURE 15
FIGURE 14
FIG. 13

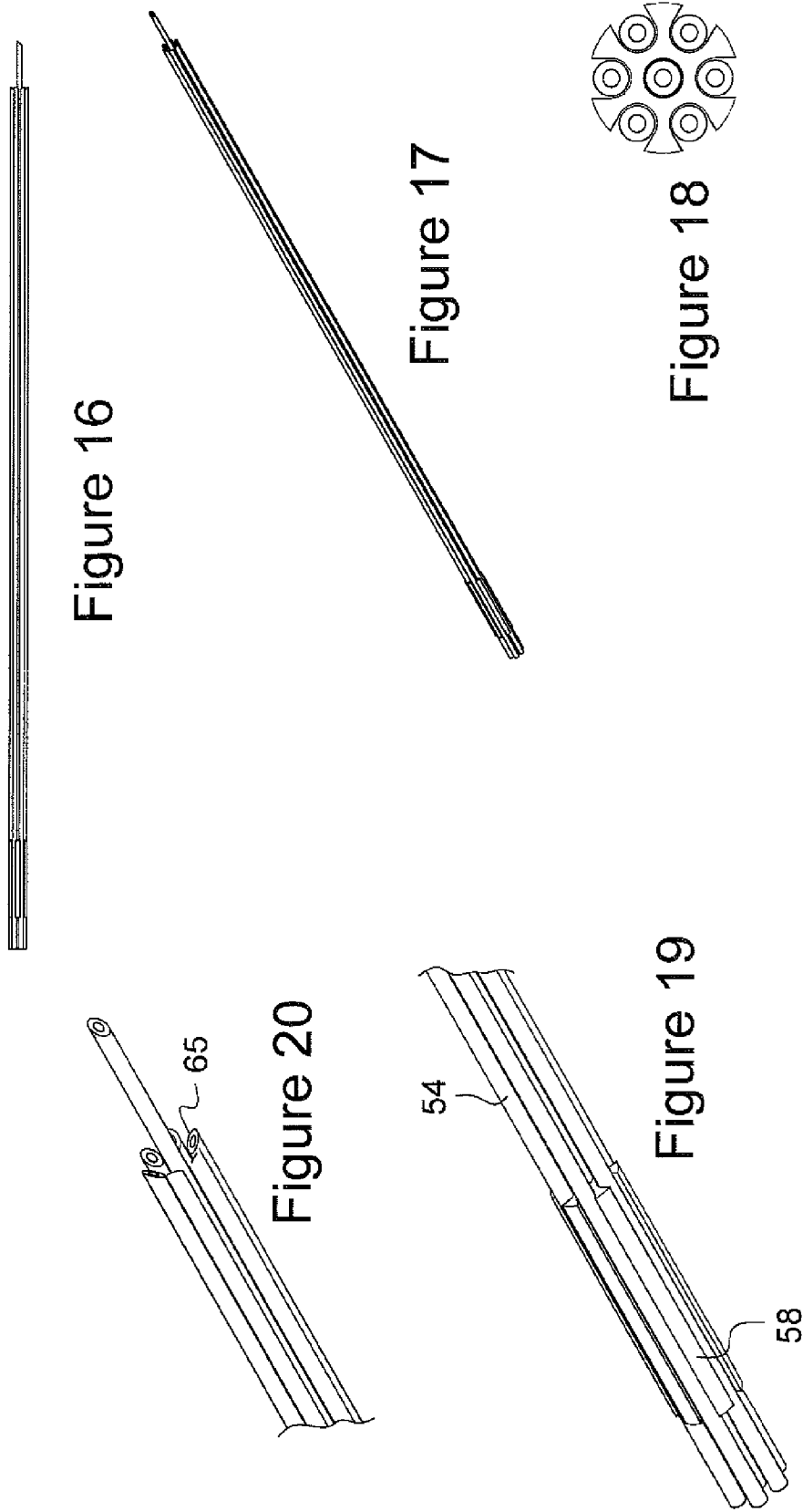

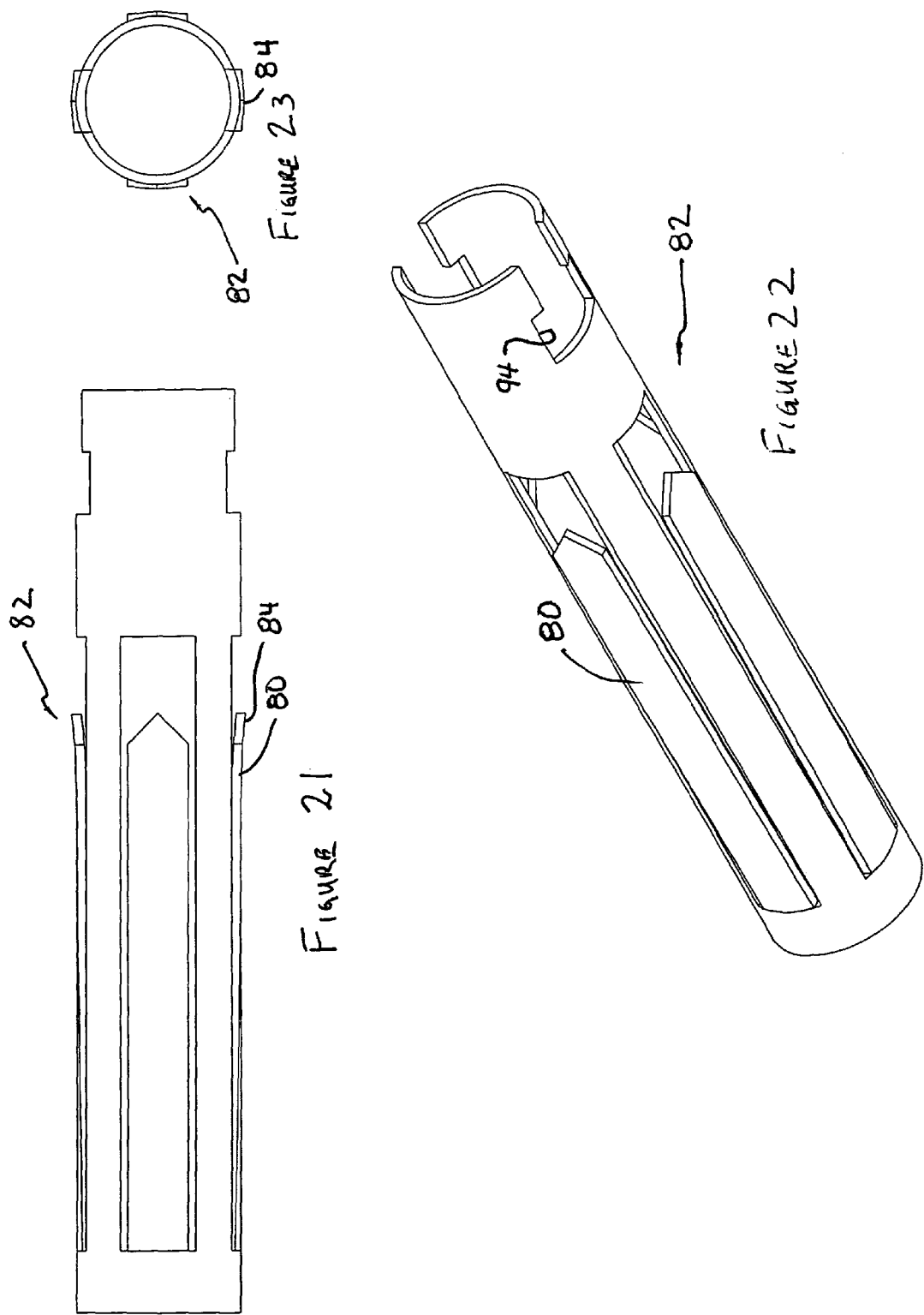

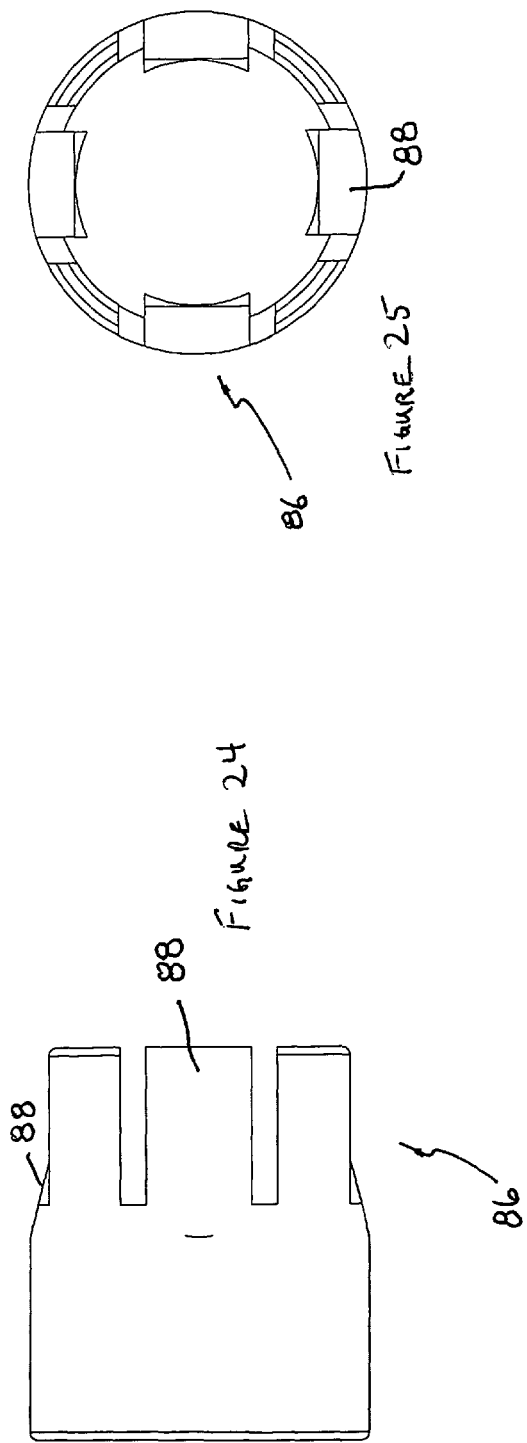
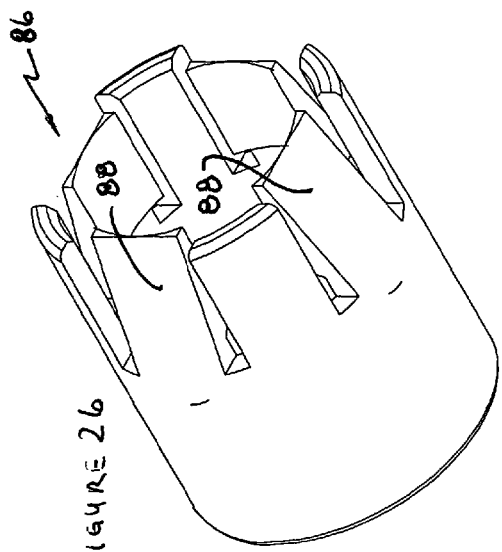

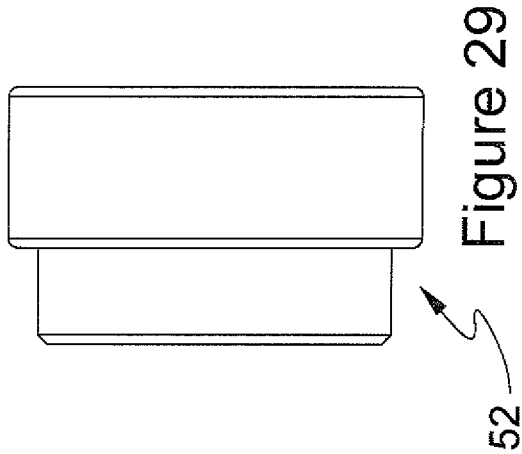
Figure 29
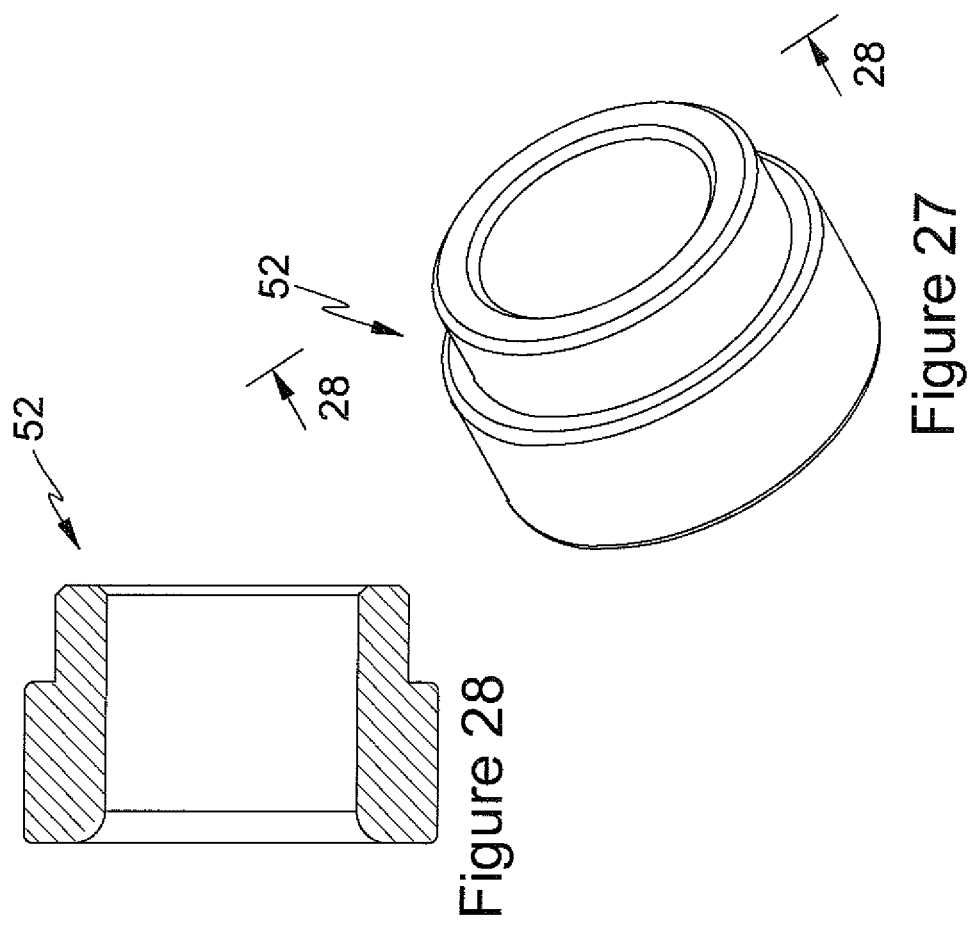
Figure 27
Figure 28

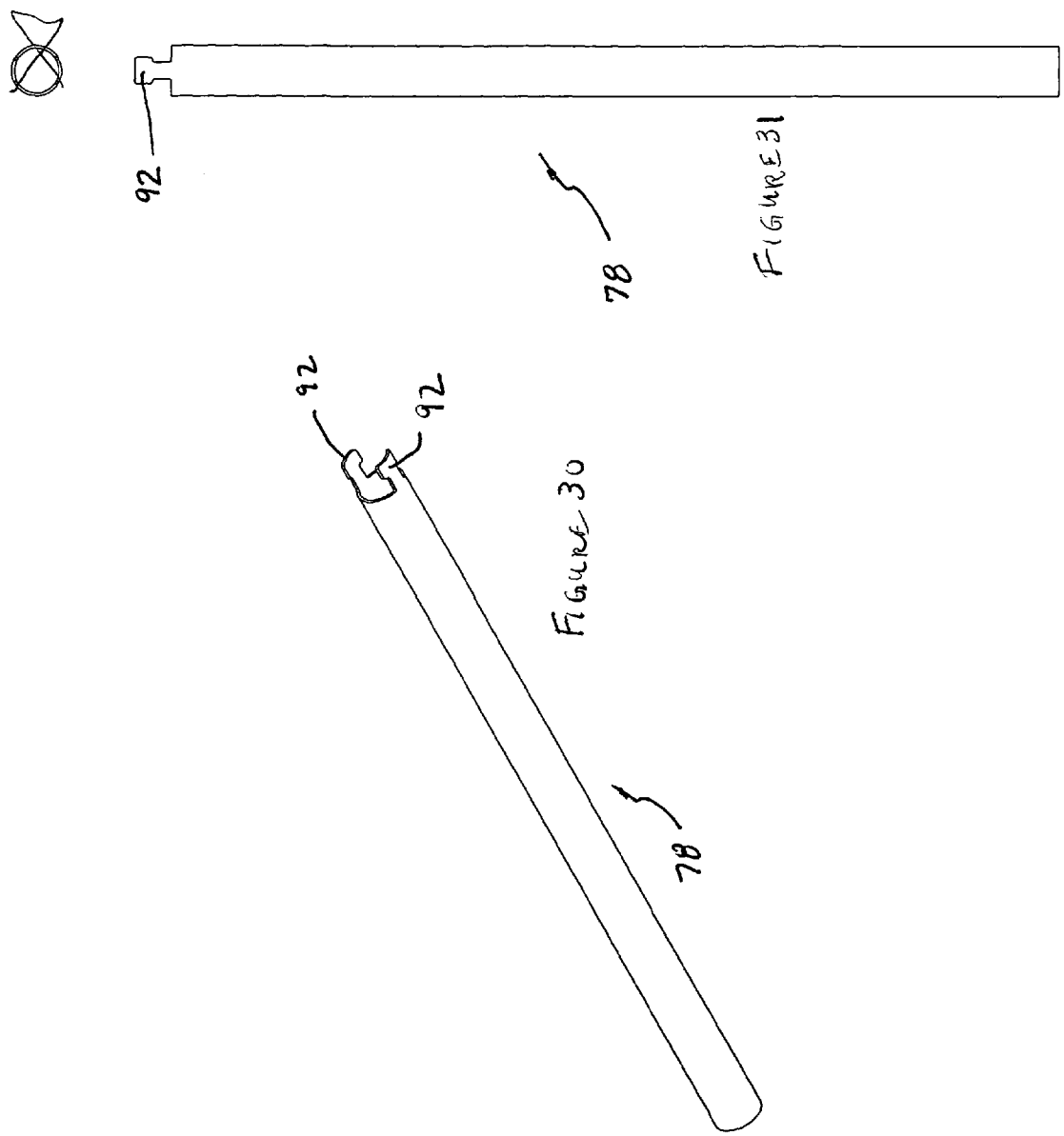

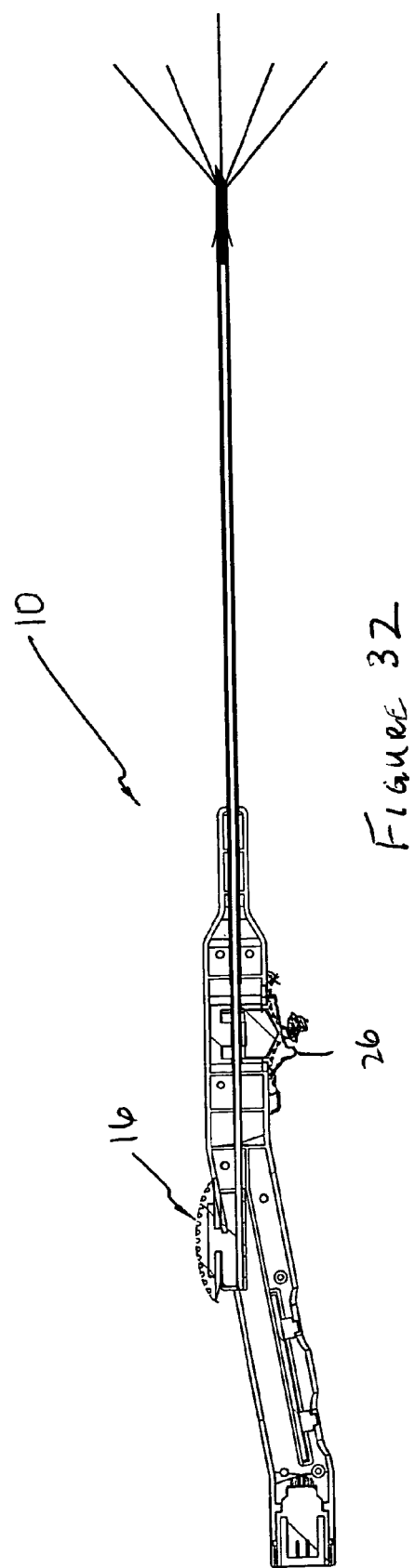

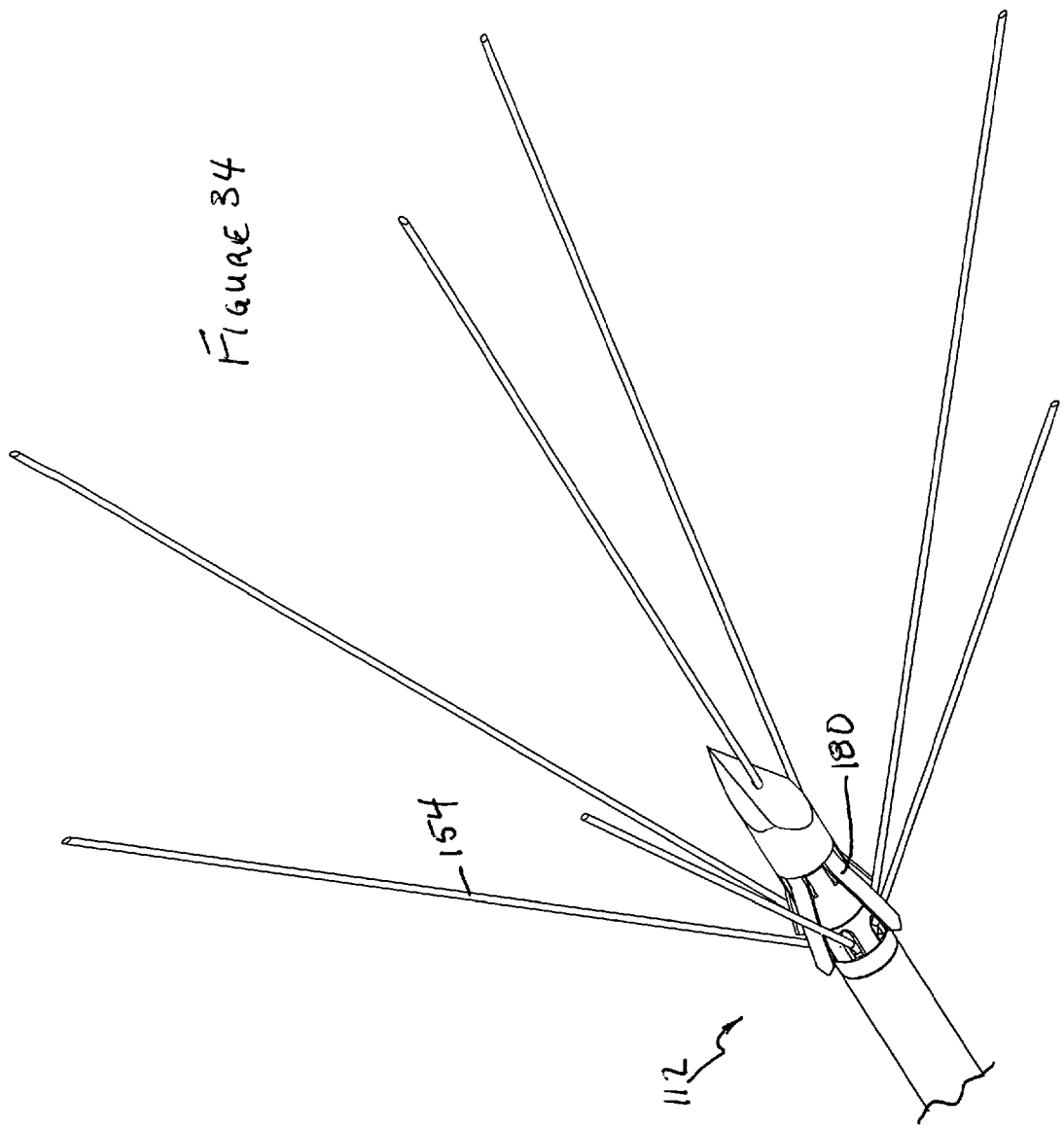

ANCHORED RF ABLATION DEVICE FOR THE DESTRUCTION OF TISSUE MASSES

CROSS REFERENCE TO RELATED APPLICATION

This application is a continuation in part of U.S. patent application Ser. No. 11/429,921, entitled "Anchored RF Ablation Device for the Destruction of Tissue Masses" filed on May 8, 2006, now U.S. Pat. No. 8,512,333, which is a continuation-in-part of U.S. patent application Ser. No. 11/173,928, entitled Radio Frequency Ablation Device for the Destruction of Tissue Masses filed on Jul. 1, 2005, now U.S. Pat. No. 8,080,009 the disclosures of which are incorporated by reference.

BACKGROUND

In the United States, approximately 230,000 women have hysterectomies annually. The primary reason for performing a hysterectomy is the presence of uterine fibroids. These fibroids grow in the wall of the uterus and may range in size up to several inches across. In the United States alone, there are more than six million women with uterine fibroid symptoms who prefer to suffer, rather than endure the risks and inconveniences associated with major surgery, especially a major surgery that results in infertility. Outside of the United States, the situation is much the same, with millions of women suffering with fibroids in need of a safe alternative to hysterectomy.

Recently, another treatment option (uterine artery embolization) has been introduced. Generally, this procedure involves embolization of the arteries which feed the urine fibroid. This results in cutting off the blood supply to the fibroid and the shrinkage of the fibroid over time. However, the unacceptably high rate of complications severely limits its appeal to patients.

Myomectomy, each generally involves the surgical removal of the fibroid through the use of classical surgical procedures, is another treatment option. However, due to its high rate of complications and long recovery time, this option is also not very appealing to patients. Typical complications involve risk of infection, relatively severe post-surgical pain, damage to the uterus and other risks normally associated with such types of surgery. Moreover, such damage may be relatively subtle and may only come to light when the uterus begins to swell in pregnancy and ruptures at a weak point created during the surgery, resulting in loss of the fetus.

Still another alternative to treat the discomfort associated with uterine fibroids is the removal of the endometrium which lines the uterus. However, this procedure results in infertility.

In an attempt to address these issues, an RF ablation probe of the type used to treat tumors in the human liver by hyperthermia has been successfully demonstrated to substantially shrink or eliminate uterine fibroids.

See, for example, U.S. Pat. No. 6,840,935 issued to Lee on Jan. 11, 2005, the disclosure of which is incorporated herein by reference. In that patent a method for treating pelvic tumors, such as uterine leiomyomata, includes inserting an ablation apparatus into a pelvic region and positioning the ablation apparatus either proximate to or into a pelvic tumor. The method further includes using a laparoscope and an imaging device, such as an ultrasound machine, to confirm the location of the pelvic tumor and placement of the ablation apparatus. An ablation apparatus with multiple needles or deployable arms that are inserted into the pelvic tumor is disclosed. The method involves delivering electromagnetic energy or other energy through the ablation apparatus to the pelvic tumor to induce hyperthermia and ablate the tumor.

The particular device disclosed for ablating the tumor in U.S. Pat. No. 6,840,935 is of the type disclosed in U.S. Pat. No. 5,728,143, issued to Gough et al. on Mar. 17, 1998. Generally, that device comprises a plurality of resilient springy RF ablation antennae, or stylets, which are preformed with a curved configuration which they assume after exiting a sharp trocar-tipped catheter. The tip of the catheter is deployed in uterine fibroid tissue to be destroyed. The stylets are then deployed into the tissue to be destroyed.

Generally, as the antennae exit the trocar tip, they pierce the tissue of the uterine fibroid along curved paths which are defined by the preformed springy shape of the stylet. The deployed stylets with their respective preformed shapes and the positions within which they are deployed thus define the ablation volume. Various shape volumes may be defined by varying the configuration of the curves which are preformed into the different springy stylets convey given trocar-pointed catheter. Such devices are manufactured by Rita Medical Systems of Mountain View, Calif. The hallmark of such devices is that the stylets assume their pre-formed configuration as they emerge from the trocar tip.

SUMMARY OF THE INVENTION

In accordance with the invention, it has been observed that difficulties are encountered in using conventional curved stylet ablation systems. More particularly, it has been discovered that uterine fibroid tissues tend to be difficult to pierce because, unlike other types of tumors, uterine fibroids are comprised of relatively hard muscle-like tissues and the curved stylets tend to deform during deployment. They are thus not very effective in piercing a uterine stylet. To a limited extent, the difficulty of piercing the fibroid with the curved stylets may be mitigated by advancing very small increments of the ablation stylet into the fibroid, applying radiation to the stylet to induce hyperthermia and degrade the physical integrity of the tissue surrounding the stylets. The stylets may then be advanced into the somewhat deteriorated and softened tissue and the application of radiation to the stylets continued to enlarge the physically deteriorated regions of the fibroid. After a time, the process of advancing the stylet to a point where resistance is encountered, and applying energy to the stylet to cause ablation of the urine fibroid tissue is repeated until penetration into the desired destruction of tissue has been achieved, or the stylets have been fully deployed.

At that point, ablation energy is applied to the stylets until the desired degree of tissue ablation has been achieved. If necessary, the trocar point may then be advanced for a repetition of the ablation operation or it may be removed and redeployed in another volume of tissue to be destroyed by the deployment of the stylets.

While the iterative advancement of the stylets, punctuated by relatively long periods of time during which advancement cannot be implemented and the surgeon must wait for the desired degree of deterioration of the tissue into which the antennae will next be advanced, will work to effectively and minimally-invasively ablate a uterine fibroid, the procedure is extremely time-consuming compared to a procedure in which antennae may be fully deployed and radiation applied to a large volume of a uterine fibroid during a single application of RF energy.

Accordingly, while the above procedure has seen some implementation, the time necessary for the procedure has made it relatively expensive and thus it is not available to many individuals. Moreover, the skill required for the performance of the procedure is relatively high, and thus few doctors are able to perform the procedure. Proliferation of this approach is not likely in view of the steep learning curve and the small number of individuals competent to perform this procedure. This has been the case, despite the effectiveness of ablation in destroying uterine fibroid tissue and the attendant absorption of necrotic tissue by the body, resulting in substantial elimination of the fibroid.

Nevertheless, in accordance with the invention, it is believed that a quick and particularly easy to implement RF ablation procedure is provided, which carries a relatively low risk of complications and a lower likelihood, under a typically encountered set of circumstances, that the uterus will be damaged and fail during a subsequent pregnancy.

In accordance with the invention an ablation element comprises an elongated cannula having a proximal end and a distal end. The cannula defines an internal lumen within the cannula and a cannula axis. A trocar point is positioned proximate the distal end of the cannula. A conductor is contained within the cannula. But conductor has a proximal end and a distal end. The distal end of the conductor is proximate the distal end of the cannula. A plurality of ablation stylets each has a proximal end and a distal end, and each coupled at the respective proximal end of the stylet to the distal end of the conductor, the stylets comprise a deflectable material and defined a substantially straight shape. The conductor together with the stylets are mounted for axial movement within the cannula. A deflection surface is positioned between the tip of the trocar point and the proximal end of the cannula. The deflection surface is configured and positioned to deflect, in response to axial movement of the stylets in a direction from the proximate end of the cannula to the distal end of the cannula, at least one of the stylets laterally with respect to the cannula axis in different directions along paths which are substantially straight for that portion of the stylet which has a suited the trocar point. These paths define an ablation volume.

The conductor may be selected from the group consisting of electrical conductors, radio frequency conductors, microwave conductors and optical conductors or light pipes.

Each of the stylets may be configured to assume a substantially straight configuration in the absence of external forces.

An ablation element further comprises a motor member or members coupled to the conductors to drive axial movement of the stylets in directions from the proximal end of the cannula to the distal end of the cannula, and from the distal end of the cannula to the proximal end of the cannula through a plurality of positions. The trocar point may be defined at the distal end of a trocar member, the trocar member having an outside surface, the cannula having an outside surface, the trocar member having a proximal end secured proximate to the distal end of the elongated cannula, and the outside surface of the cannula and the outside surface of the trocar point defining a trocar surface. The trocar member acts as a stylet mandrel to deflect the stylets, which may be electrodes, along paths which are substantially straight after the stylets exit the mandrel into the tissue to be ablated.

The deflection surface comprises a number of ramps defined proximate the proximal end of the trocar point, the distal ends of the stylets being positionable proximate to the ramps and within the trocar surface.

The conductor and the stylets are electrical conductors, and each of the stylets may be configured to assume a substantially straight configuration in the absence of external forces.

The deflection surface comprises a plurality of channels guiding the distal ends of the stylets to the ramps. The cannula may be secured to the trocar member with the outside surface of the cannula proximate to the outside surface of the trocar member.

The ablation element also comprises an anchor mounted for movement between an internal position disposed within the trocar surface and an anchoring position extending laterally from the trocar surface through points external of the lumen; and a drive member disposed within the lumen and coupled to the anchor to drive the anchor between the internal position and the anchoring position.

The anchor comprises at least two pointed members mounted for movement in directions which have vector components which extend away from the axis of the cannula and away from each other. The pointed members also preferably extend in a direction with a vector component that extends in a direction opposite to the direction in which the trocar point extends.

The conductors are driven by a drive mechanism which allows the conductors to move independently. The conductors have a length, a width and a thickness, the width being greater than the thickness, and terminate in a point oriented to allow deflection by the deflection surface. The conductors extend in different directions when they exit the deflection surface and extend to a variable extent.

The conductors are driven by a drive circuit which varies the amount of energy supplied to the stylets and/or the length of the stylets and/or the length of the time during which power is supplied to the stylets and/or the angular orientation of the ablation element (through the variation of ramp deflection angle.

The parameters of stylet length, stylet power, stylet actuation time and/or angular orientation may be controlled by a computer in response to a computer program having an input comprising feedback information from the tissue area being operated on and/or a preset program.

The anchor is mounted for movement between an internal position disposed within the trocar surface and an anchoring position extending laterally from the trocar surface through points external of the lumen. The drive member may be disposed within the lumen and coupled to the anchor to drive the anchor between the internal position and the anchoring position. The desired motive force for advancing the stylets and/or optional anchors may be provided by a finger operated slidably mounted gripping surface which the surgeon uses to manually advance the conductor and the stylets attached to the end of the conductor. The gripping surface may be slidably mounted on a handle within which the proximal end of the trocar is mounted. The anchor comprises at least two pointed members mounted for movement in directions which have vector components which extend away from the axis or the cannula and away from each other.

As alluded to above, the front end of the inventive catheter is a trocar point defined at the distal end of a trocar member. The trocar member has an outside surface. The cannula has an outside surface, and the trocar member has a proximal end secured proximate to the distal end of the elongated cannula. The outside surface of the cannula and the outside surface of the trocar point define the trocar surface. The trocar member bears a plurality of deflection surfaces. The deflection surface comprises a number of ramps defined within the trocar member. The distal ends of the stylets are positionable proximate to the deflection surfaces and within the trocar surface.

In accordance with a particularly preferred embodiment of the invention, it is contemplated that a graphical user interface and a pair of electrical switches, for example a joystick and a pushbutton, will be used to switch between operating parameter options for the inventive catheter which are displayed on a graphical user interface (or other information conveying device such as an audio cue generator). The surgeon navigates a menu, for example, using a joystick looking at or hearing an electronically generated audio signal, such as a voice, presenting various options and selects the desired option by pushing the electrical switch. In principle, this can be done on a single switch incorporating joystick and pushbutton features.

Optionally, the electrical switches which operate the system may be recessed partially or fully in order to minimize the likelihood of unintentional actuation. Additional protection may be provided by requiring two motions within a relatively short period of time in order to achieve a change in the control of the system.

In accordance with a particularly preferred version of the invention, this is achieved by having a human voice present options and acknowledge instructions, which may be given to the system orally using voice recognition technology. This allows the surgeon to operate without having to look away from visual displays guiding the operation, the patient, instruments and so forth, thus removing potential losses of information. A display simultaneously displays all relevant information to provide a quicker provision of information to the surgeon.

In accordance with the invention it is contemplated that laser manufacturing techniques may be used to manufacture the anchors and perhaps the anchor deflection surfaces.

Preferably, the point of the trocar is milled to a point with three surfaces. Stylets are milled in the manner of a hypodermic needle. Stylets are oriented to cooperate with the deflection surfaces which deflect them. A cooperating low friction insulator ring, for example, made of Teflon, cooperates with the deflection surfaces to deflect hypotube electrode stylets.

The present invention contemplates the use of rearwardly deployed anchoring stylets which act as retractable barbs for maintaining the position of the trocar point during forward deployment of the radiofrequency (RF) electrode ablation stylets.

In accordance with the present invention, a stylet operating member, optionally a stylet push member, which may be a tube, is positioned on one side of a tubular compression/tension operator, for example on the inside of the compression/tension operator. Similarly, in accordance with the present invention, and anchor member operating member, optionally an anchor pull member, which may be a tube, is positioned on the other side of a tubular compression/tension operator, for example on the outside of the compression/tension operator. Such outside placement is particularly advantageous in the case where the anchoring member is of relatively wide dimension and large size.

In accordance with a preferred embodiment of the invention, the compression tension operator is secured at the proximal end to the handle of the ablation instrument and at the distal end to the anchoring member deflection surface and the hypotube electrode stylet deflection surface.

The invention contemplates a plurality of hypotube electrode stylets which are bound together as a unitary structure and advanced by a single push tube or wire.

It is also contemplated that the inventive instrument will include channels for flushing clean. In accordance with the inventive system, the frequency with which flushing should be performed is minimized through the use of a trocar front face which is substantially closed (except for a single undeflected hypotube which exits the front face of the trocar) and providing for exit of hypotubes through the cylindrical side wall of the trocar point.

In accordance with a particularly preferred embodiment of the invention, the anchor member is separate from the anchor push tube, and is connected it to by mating or other interlocking structure.

Deflection surfaces for both the hypotube stylets and anchors are selected to result in strains in the range of 2% to 8%, preferably about 4%, for example 3.5% to 4.5%, which represents a reasonable compromise between instrument longevity and a relatively large amount of deflection.

An insulation sleeve is positioned between the anchors and the hypotube stylets in order to allow separate electrical actuation and ablation with either or both of the anchors and the hypotube stylets.

The hypotube stylets contain thermocouples which are used to measure the temperature of ablated tissue, thus ensuring that the tissue will be raised to the correct temperature for a sufficient period of time to ablate tissue resulting in the creation of necrotic tissue which may be absorbed by the body.

In accordance with the preferred embodiment of the invention, hypotube stylets are deployed forwardly or distally while anchors are deployed in a proximal direction or rearwardly. Alternatively, the hypotube stylets may be deployed in a proximal direction or rearwardly, while anchors are deployed forwardly or distally.

As compared to a conventional hysterectomy, the present invention is directed to a device for the treatment of uterine fibroids and other tissue masses that meets the needs of women by conserving the uterus and reducing recovery time from 6-8 weeks to 3-10 days.

BRIEF DESCRIPTION OF THE DRAWINGS

FIG. 5 is a plan view of the catheter with seven hypotube ablation electrodes and four anchors deployed;

FIG. 6 is a perspective view of the catheter structure of FIG. 5;

FIG. 13 is a perspective view illustrating a core for holding a plurality of hypotubes;

FIG. 14 is a side plan view illustrating a core for holding a plurality of hypotubes;

FIG. 15 is a rear view illustrating a core for holding a plurality of hypotubes;

FIG. 16 is a side plan view illustrating a core holding a plurality of hypotubes;

FIG. 17 is a perspective view illustrating a core holding a plurality of hypotubes;

FIG. 18 is a rear view illustrating a core holding a plurality of hypotubes;

FIG. 19 is a perspective detailed view illustrating a core holding a plurality of hypotubes;

FIG. 20 is a perspective detailed view illustrating the tips of a plurality of hypotubes when they are being held in a core as illustrated in FIG. 19;

FIG. 21 is a side plan view illustrating a rearward anchoring member;

FIG. 22 is a perspective view illustrating a rearward anchoring member;

FIG. 23 is an end view illustrating a rearward anchoring member;

FIG. 24 is a plan view illustrating a rearward anchoring member;

FIG. 25 is an end view illustrating an anchor deflecting mandrel member;

FIG. 26 is a perspective view illustrating an anchor deflecting mandrel member;

FIG. 27 is a perspective view of an insulating ring for insulating the hypotube electrodes from the anchors;

FIG. 28 is a cross-sectional view of an insulating ring for insulating the hypotube electrodes from the anchors along lines 28-28 of FIG. 27;

FIG. 29 is a side view of the insulating ring for insulating the hypotube electrodes from the anchors;

FIG. 30 is a perspective view illustrating the anchor push tube;

FIG. 31 is a side plan view illustrating the anchor push tube in accordance with the present invention;

FIG. 32 is partially cross-sectional view, similar to FIG. 1 illustrating the inventive instrument with anchors and hypotubes deployed;

FIG. 34 is a detail perspective view similar to FIG. 33 illustrating full deployment of hypotubes and anchors in an alternative embodiment of the invention.

DETAILED DESCRIPTION OF THE BEST MODE

Figure 1:
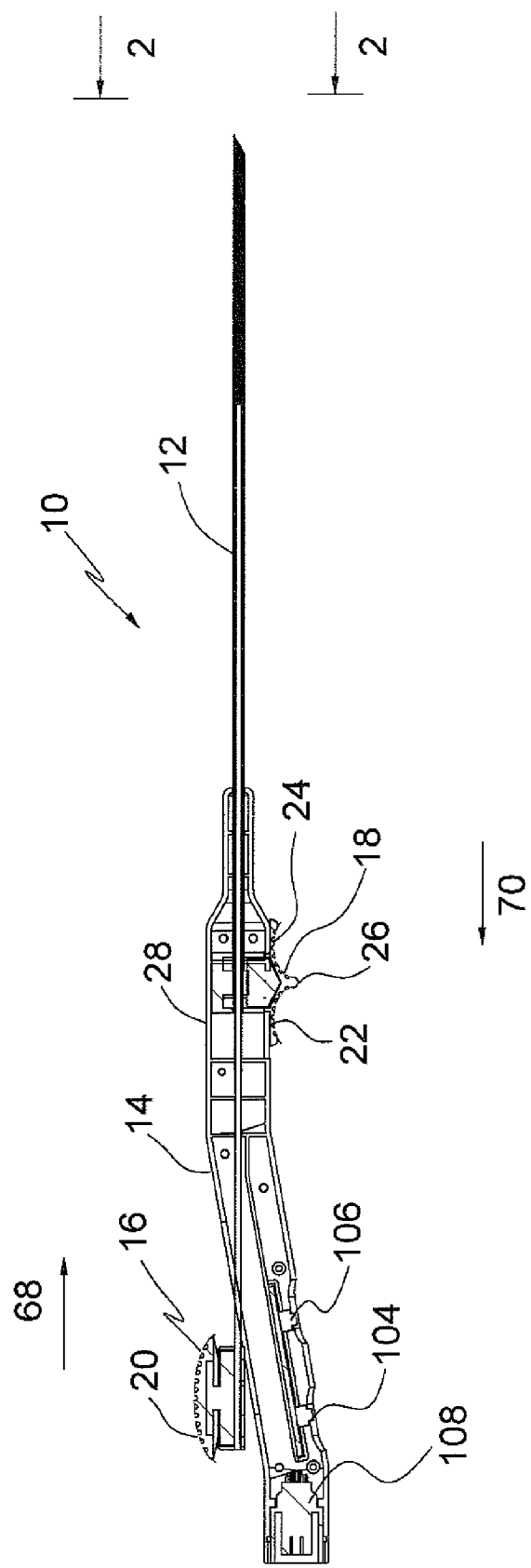
FIG. 1 is a plan view of the multiple antenna ablation device of the invention with the cover removed and partially in cross-section to illustrate its operation.

Referring to FIG. 1, an ablation instrument 10 constructed in accordance with the present invention is illustrated. Instrument 10 comprises a catheter portion 12 and a handle portion 14. Ablation instrument 10 is illustrated with one of the two mating handle halves removed and partially in cross section, in order to reveal its internal parts and workings in connection with the following description.

Figure 2:
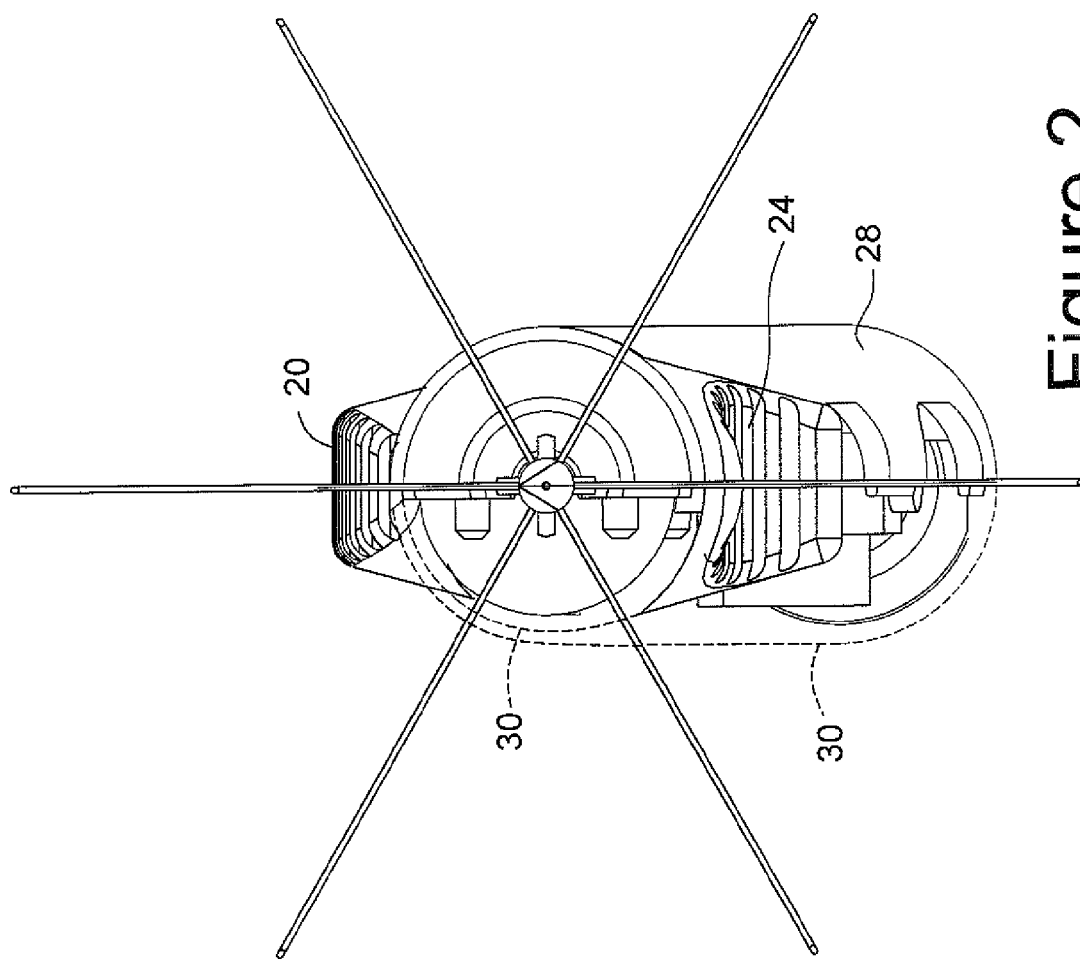
FIG. 2 is a front view of the inventive probe with anchor system of the device along lines 2-2 of FIG. 1, but illustrating the instrument after deployment of the anchor.

Referring to FIGS. 1 and 2, the inventive ablation instrument 10 is illustrated in the fully retracted position suitable for advancement of catheter portion 12 into tissue, for example, tissue to be subjected to ablation by being treated with radiofrequency energy. In this position, the catheter 12 present a simple thin smooth pointed surface well-suited to penetrate healthy tissue while doing minimal damage. At the same time, the sharpness of the point and the relatively stiff, though somewhat flexible, nature of catheter 12 enables accurate steering of the point and control of the path of penetration. In the case of the treatment of uterine fibroids, such steering is achieved largely by manipulation of the uterus coupled with advancement of the catheter 12.

Handle portion 14 includes a pair of actuators namely a stylet actuator 16 and an anchoring actuator 18. Stylet actuator 16 includes a serrated surface 20. Anchoring actuator 18 includes a pair of serrated surfaces, namely an anchor retraction surface 22 and an anchor deployment surface 24. The application of relatively great force is facilitated by a wall 26, against which the thumb or other finger of the surgeon may bear during the respective deployment and retraction phase of an operation performed using the inventive ablation instrument 10.

Stylet actuator 16 and anchoring actuator 18 are supported within handle portion 14. Handle portion 14 comprises a left housing half 28 and a right housing half 30 symmetrical in shape to left housing half 28, as illustrated in FIG. 2.

Figure 3:
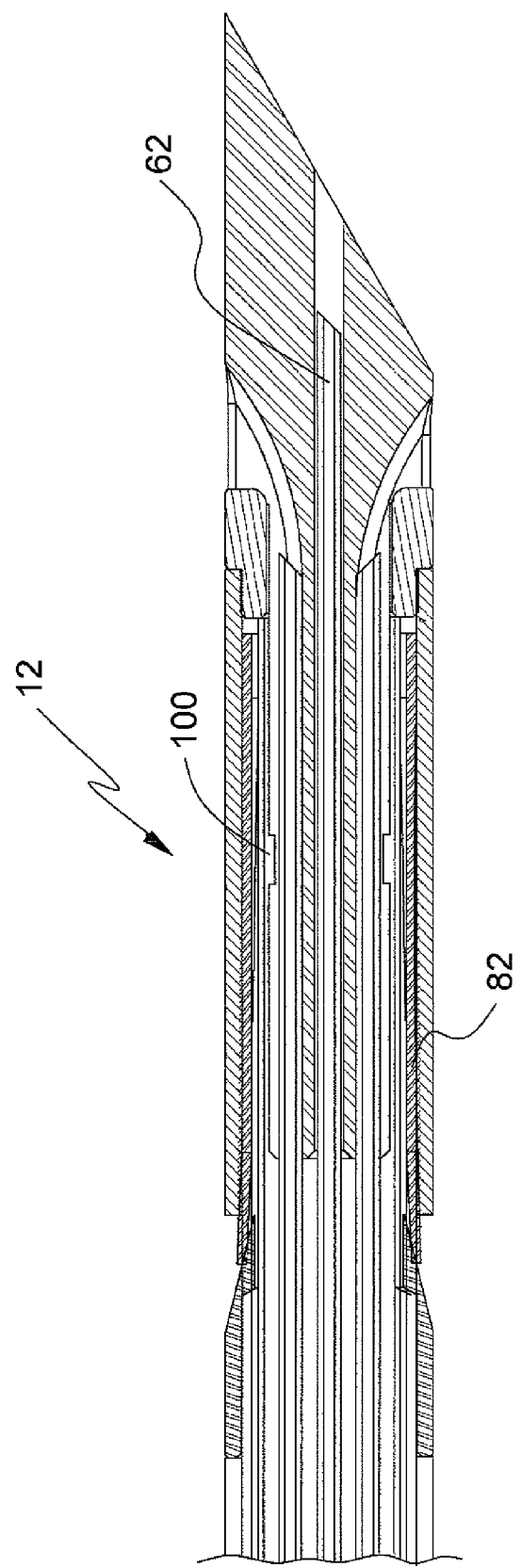
FIG. 3 is a cross-sectional view of the tip of the catheter constructed in accordance with the present invention.
Figure 4:
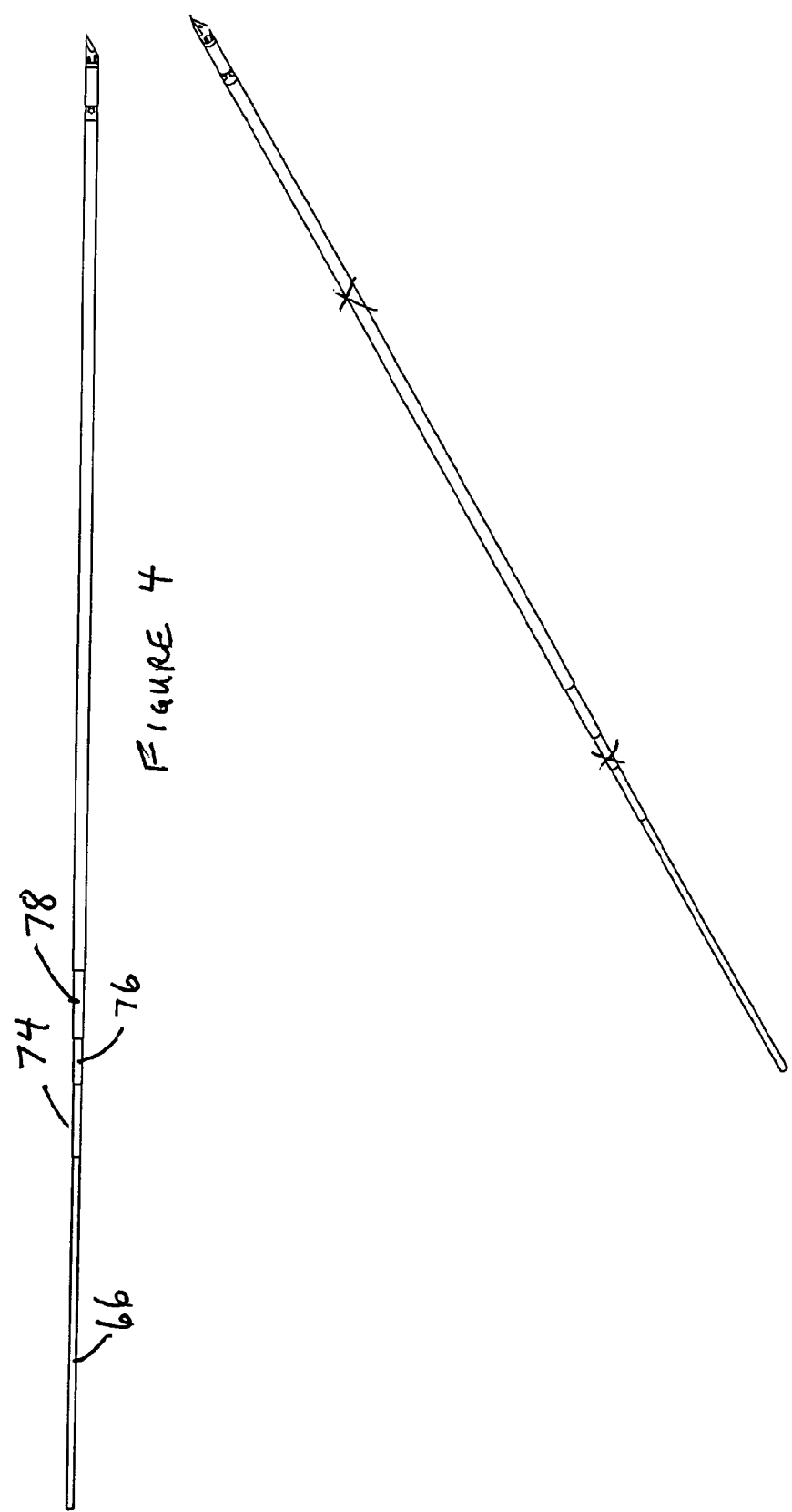
FIG. 4 is a plan view of the apparatus of the present invention with anchors and ablation hypotubes not deployed.

As illustrated in FIGS. 1, 3 and 4, the inventive ablation instrument may be configured in the undeployed state. Alternatively, as illustrated in FIGS. 2, 5, 6 and 7, the inventive ablation instrument 10 may be configured either the anchors or the ablation stylets in a deployed state, or as illustrated in FIGS. 2, 5, 6 and 7 with anchors and stylets both fully deployed.

Figure 7:
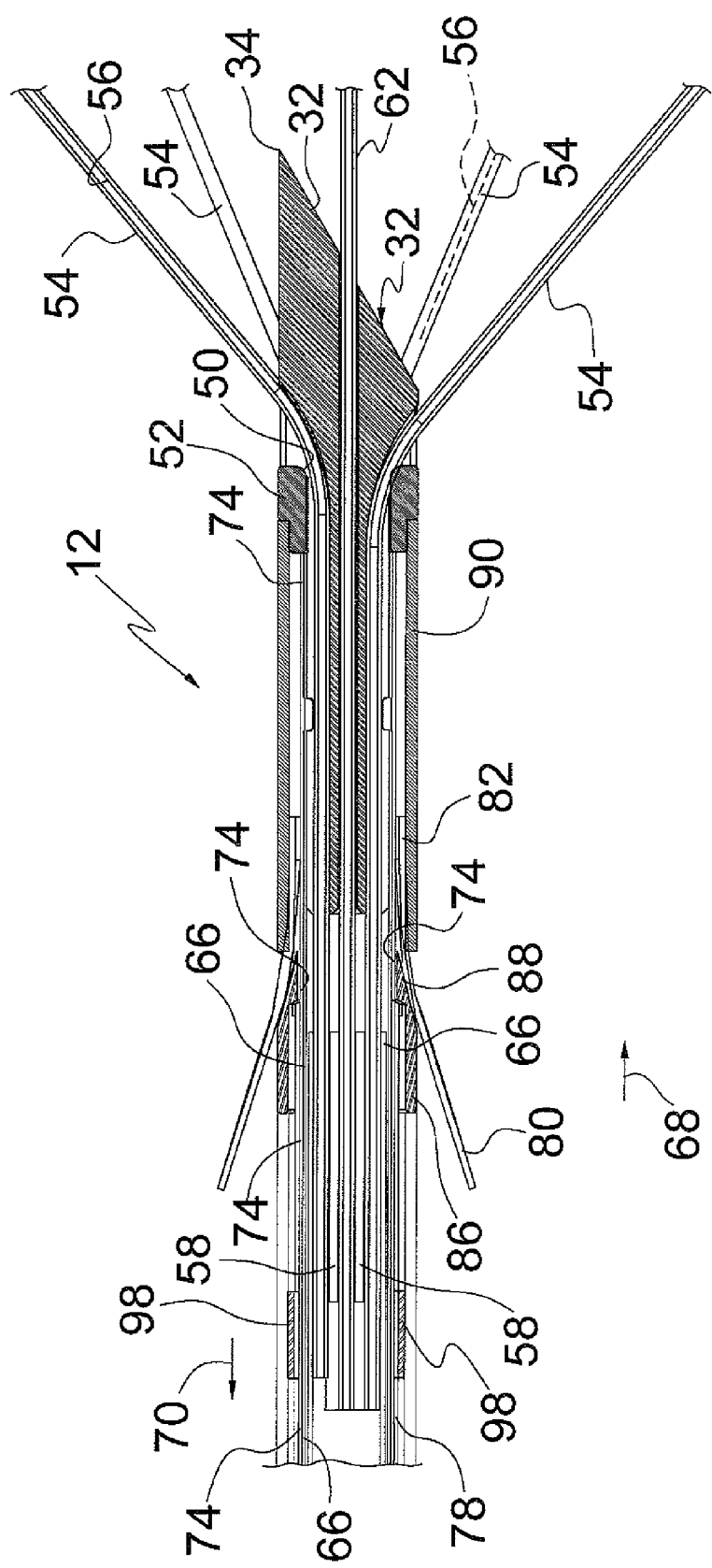
FIG. 7 is a cross-sectional view illustrating deployed hypotubes and anchors.
Figure 8:
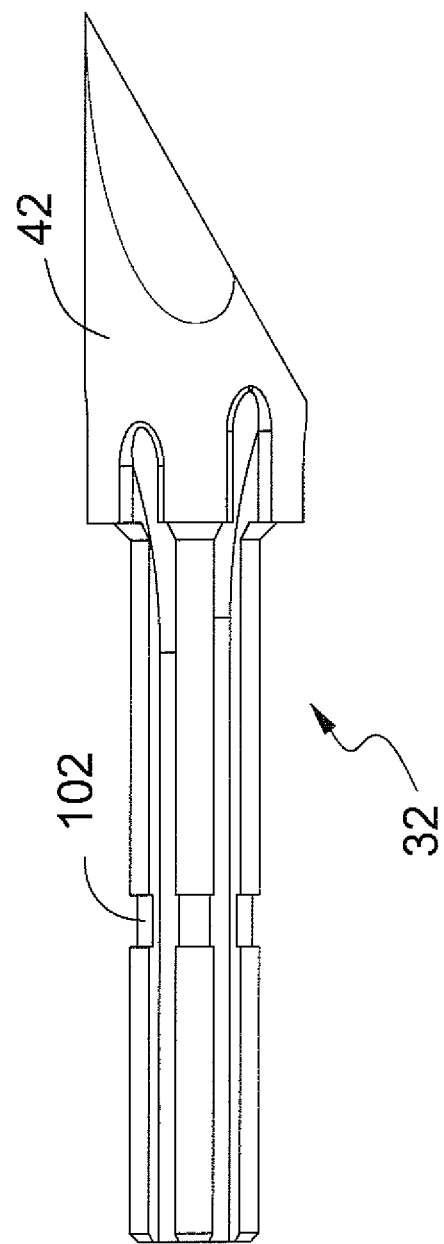
FIG. 8 is a plan view illustrating a trocar point with deflection surfaces for guiding hypotubes.

Referring to FIG. 7, ablation instrument 10 is terminated in a trocar 32, which defines a pointed tip 34. Trocar 32 also functions as an electrode mandrel to deflect the tissue ablation stylets in various directions, as appears more fully below. Trocar 32 is illustrated in FIGS. 8-12. Trocar 32 has a pointed tip 34, defined by bottom surface 36 and side surfaces 38 and 40, as illustrated most clearly in FIG. 8. Surfaces 36, 38 and 40 ground into the distal portion 42 of trocar 32. Trocar 32 also includes a central channel 44 which extends through the length of trocar 32 and is centered on the central axis of trocar 32.

Figure 9:
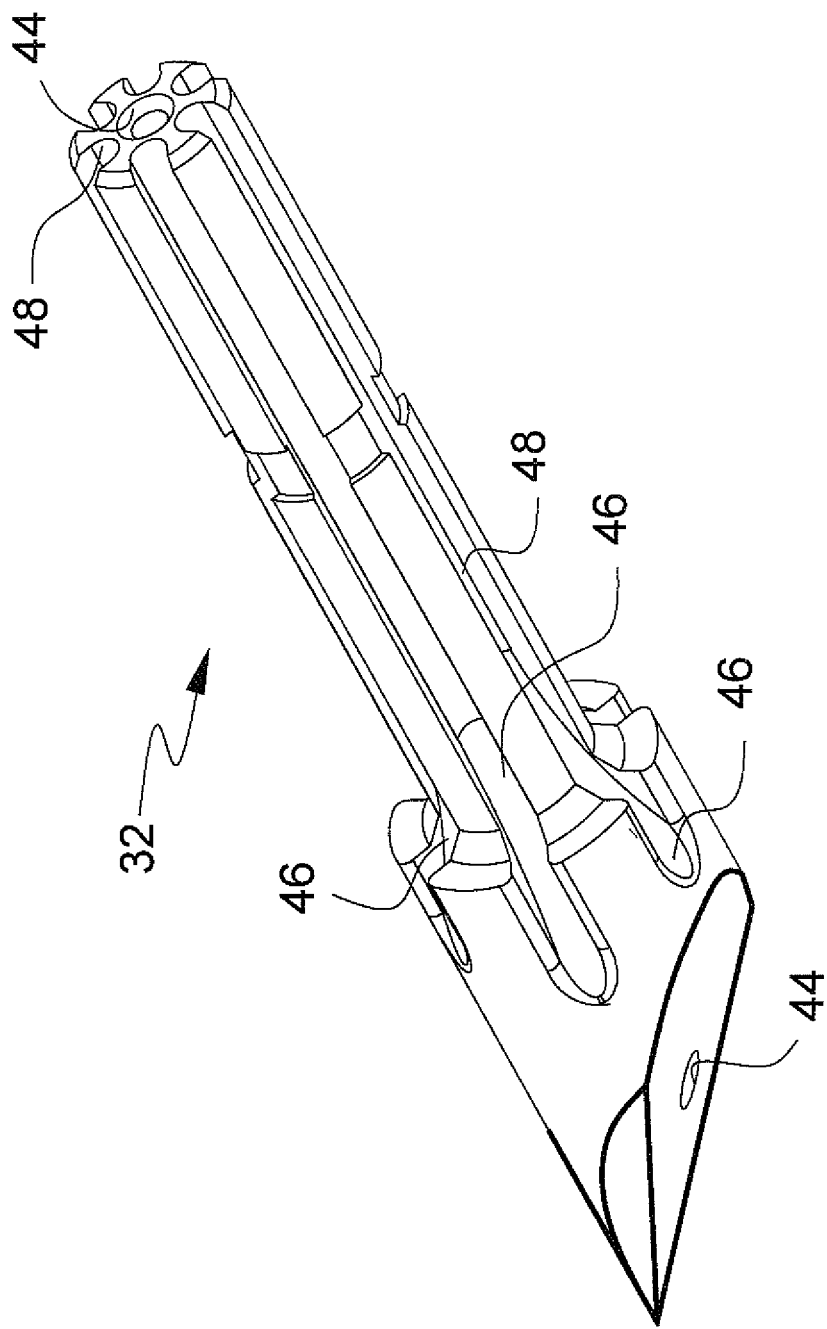
FIG. 9 is a perspective view illustrating a trocar point with deflection surfaces for guiding hypotubes.
Figure 10:
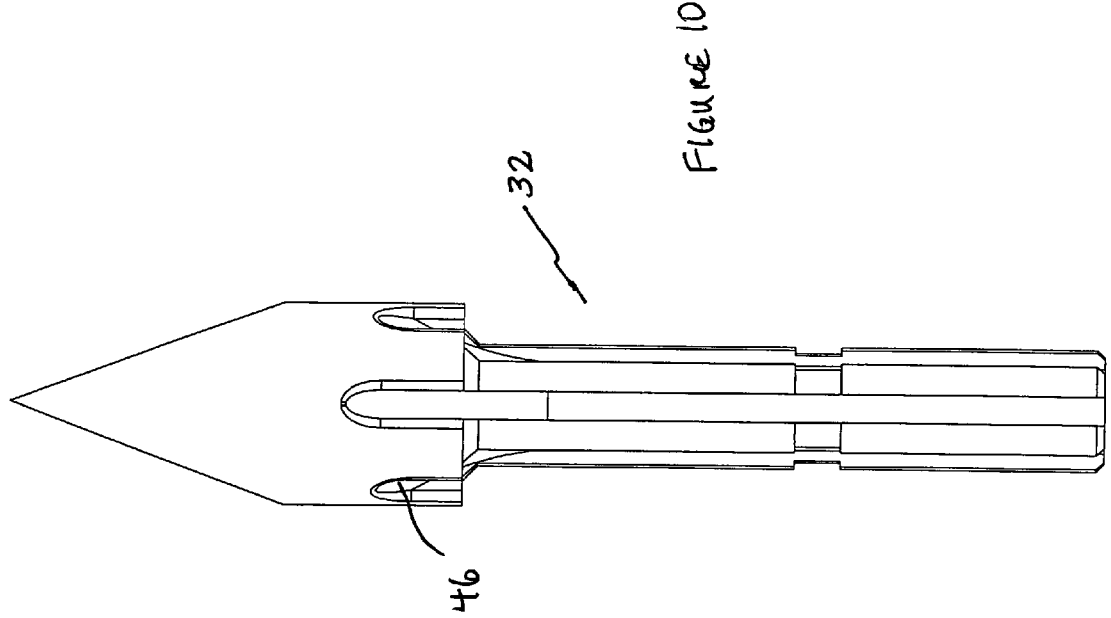
FIG. 10 is a top plan view illustrating a trocar point with deflection surfaces for guiding hypotubes.
Figure 11:
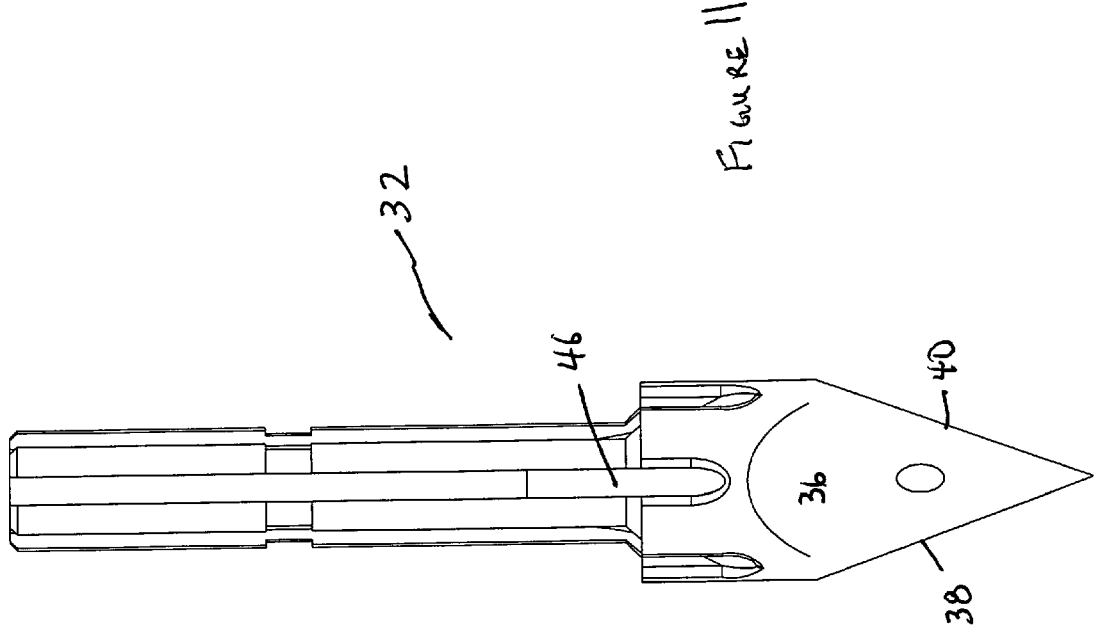
FIG. 11 is a bottom plan view illustrating a trocar point with deflection surfaces for guiding hypotubes.
Figure 12:
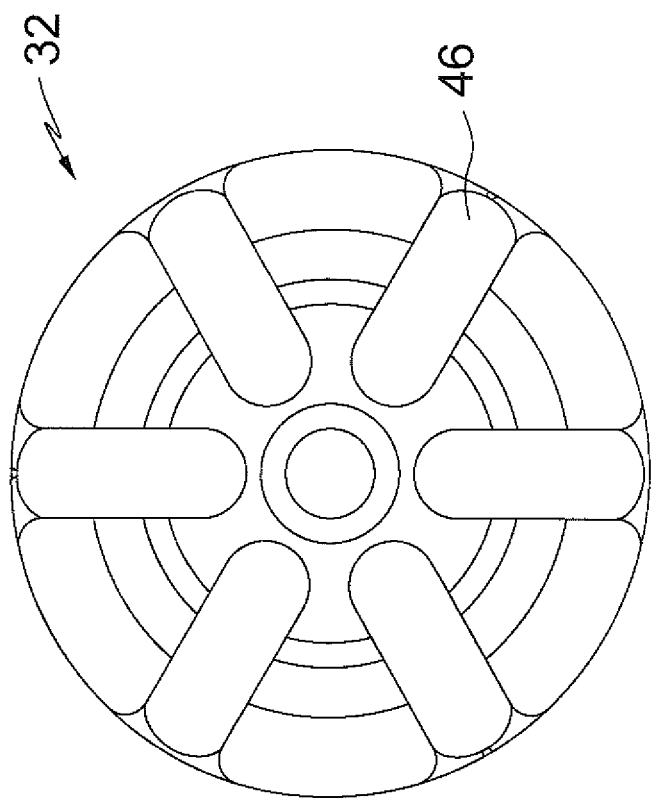
FIG. 12 is a rear view illustrating a trocar point with deflection surfaces for guiding hypotubes.

A plurality of deflection surfaces 46 are positioned at the end of longitudinal grooves 48, as illustrated in FIG. 9. These surfaces 46 are configured to gently bend the flexible hypotubes which are excited with radiofrequency energy during the ablation of uterine fibroid tissue, causing them to exit catheter 12 and follow substantially straight paths through the tissue to be ablated. During this deflection, the action of deflection surfaces 46 is complemented by the inside curved surface 50 of insulative Teflon deflector ring 52.

In accordance with an especially preferred embodiment of the invention, stylets 54 are made of a nickel titanium alloy instead of stainless steel. In this case, the configuration of deflection surfaces 46 is shaped to maximize the deflection without over straining the nickel titanium alloy material of the stylets. More particularly, in accordance with the preferred embodiment of the invention, surfaces 46 are configured to result in a strain less than eight percent. Strains in the range of 2%-8% will work with strains in the range of about 4%, for example 3.5% to 4.5%, representing an easy to implement commercial solution. Less than 2% strain does not provide appreciable bending with today's technology. Higher performance may be obtained by maintaining a deflection angle which results in a strain of 6-7%. Configuring surface 46 to result in strains approaching 8%, for example 7.5% will maximize deflection and flexibility in design of ablation volume, but will tend to result in quicker degradation of hypotube stylets 54. However, if a particular procedure does not involve a great number of ablations, or the use of several disposable ablation catheters 10 is acceptable, such devices under certain circumstances do present advantages.

The deflection of a plurality of hypotubes 54 is illustrated in FIG. 7. Hypotubes 54 are flexible hollow tubes made of steel or nickel titanium alloy. Hypotubes 54, as well as all other steel parts of the inventive ablation device 10, are preferably, for economic and/or performance reasons, made of stainless steel or other high quality steel, except as indicated herein. The tubes define an internal volume 56 which contains a wire thermocouple, which performs the function of measuring the temperature of the ablated tissue which, over time, allows control of the ablation operation and ensures that the ablated tissue will become necrotic. In FIG. 7, the thermocouples 56 are shown in only one of the tubes for purposes of clarity of illustration.

Hypotubes 54 slidably move in longitudinal grooves 48. Hypotubes 54, which function as ablation electrodes, are mounted on a needle core 58, illustrated in FIGS. 13-15. Needle core 58 includes a plurality of longitudinal grooves 60. Each of six hypotubes 54 is mounted in its respective longitudinal groove 60 and secured in groove 60 by friction or through the use of an adhesive. A seventh hypotube 62 is mounted in a central axial bore 64. The assembly of hypotubes 54 and 62 in needle core 58 is illustrated in FIGS. 16-18. The mounting of hypotubes 54 in needle core 58 is illustrated most clearly in perspective in FIG. 19.

As illustrated most clearly in FIG. 20, hypotubes 54 are preferably oriented with the flat surfaces 65 of their points oriented to slidingly cooperate with deflection surfaces 46 during deployment of the hypotubes. This is done by having the pointed tips of hypotubes 54 radially displaced from the center of catheter 12, which prevents the pointed tips of the hypotubes from digging into deflection surfaces 46.

A flexible steel electrode push tube 66 is disposed around and secured to needle core 58 with the needles mounted in it. Sliding movement of the hypotubes 54 in longitudinal grooves 48 is achieved by movement of electrode push tube 66. Movement in direction 68 causes the deployment of hypotubes 54 and 62. Movement in direction 70 causes retraction of the hypotubes.

Referring to FIGS. 5 and 7, a flexible steel electrode mandrel tube 74 is disposed around and over electrode push tube 66. Flexible steel electrode mandrel tube 74 allows electrode push tube 66 to freely slide within it. This is achieved, despite the relatively large area of the tubes, because the facing surfaces of the tubes are both smooth and because there is a small gap between their facing surfaces, thus minimizing friction. Such gaps allow provision for flushing the instrument clean with water, as is done with prior art devices. A flexible plastic tubular insulative member 76 is disposed around and over electrode mandrel tube 74.

Insulative member 76 isolates electrical radiofrequency ablation energy (carried by push tube 66 for exciting hypotubes 54 and 62) from anchor push tube 78. This allows electrical ablation energy to be optionally applied to anchor push tube 78 to independently cause the anchors 80 on anchor member 82 to apply ablation energy to a different volume than that which is ablated by the electrode stylets 54 and 62. Anchor member 82 is illustrated in FIGS. 21-23. Anchors 80 are cut using a laser from a steel tube to form steel anchor member 82. Each anchor 80 has a tip 84 which is bent radially outwardly to facilitate deflection over anchor mandrel 86 in response to movement of anchor member 82 in the direction of arrow 70.

Anchor mandrel 86 is illustrated in FIGS. 24-26. Anchor mandrel 86 incorporates a number of deflection surfaces 88, as illustrated most clearly in FIGS. 7 and 26. In accordance with an especially preferred embodiment of the invention, anchor member 82, and thus anchors 80, are made of a nickel titanium alloy instead of stainless steel. Nickel titanium alloy is a preferred material for both anchors 80 and stylets 54.

The configuration of deflection surfaces 88 is shaped to maximize the deflection without over-straining the nickel titanium alloy material of the anchors. More particularly, in accordance with the preferred embodiment of the invention, surfaces 88 are configured to result in a strain less than eight percent. Strains in the range of 2-8% will work with strains in the range of about 4%, for example 3.5 to 4.5%, are less rigorously 3% to 5%, representing an easy to implement commercial solution. Higher performance may be obtained by maintaining a deflection angle which results in a strain of 6-7%. Configuring surface 88 to result in strains approaching 8%, for example 7.5% will maximize deflection and flexibility in design of ablation volume, but will tend to result in quicker degradation of anchors 80. However, if a particular procedure does not involve a great number of ablations, or the use of several disposable ablation catheters 10 is acceptable, such devices under certain circumstances do present advantages.

The structure of the distal end of catheter portion 12 is completed by a steel anchor cover 90, which is supported on, surrounds and is secured to insulating ring 52 whose structure is illustrated in FIGS. 27-29. During deflection, anchors 80 pass between deflection surfaces 88 and the inside surface of steel anchor cover 90.

Anchor push tube 78, illustrated in FIGS. 30 and 31 includes a pair of keys 92 which are shaped like the letter T. Keys 92 mate with slots 94 in anchor member 82. Anchor member 82 and anchor push tube 78 thus act as a unitary member during deployment and retraction of anchors 80, in response to sliding motion of anchor member 82 and anchor push tube 78.

The structure of catheter 12 is completed by outer tube 96 which is secured to handle 14 at one end and secured to a tubular slip ring 98 which slides over anchor push tube 78.

FIG. 1 illustrates the relative positions of anchoring actuator 18, and stylet actuator 16 before deployment of anchors and stylets. This corresponds to FIG. 4.

Figure 33:
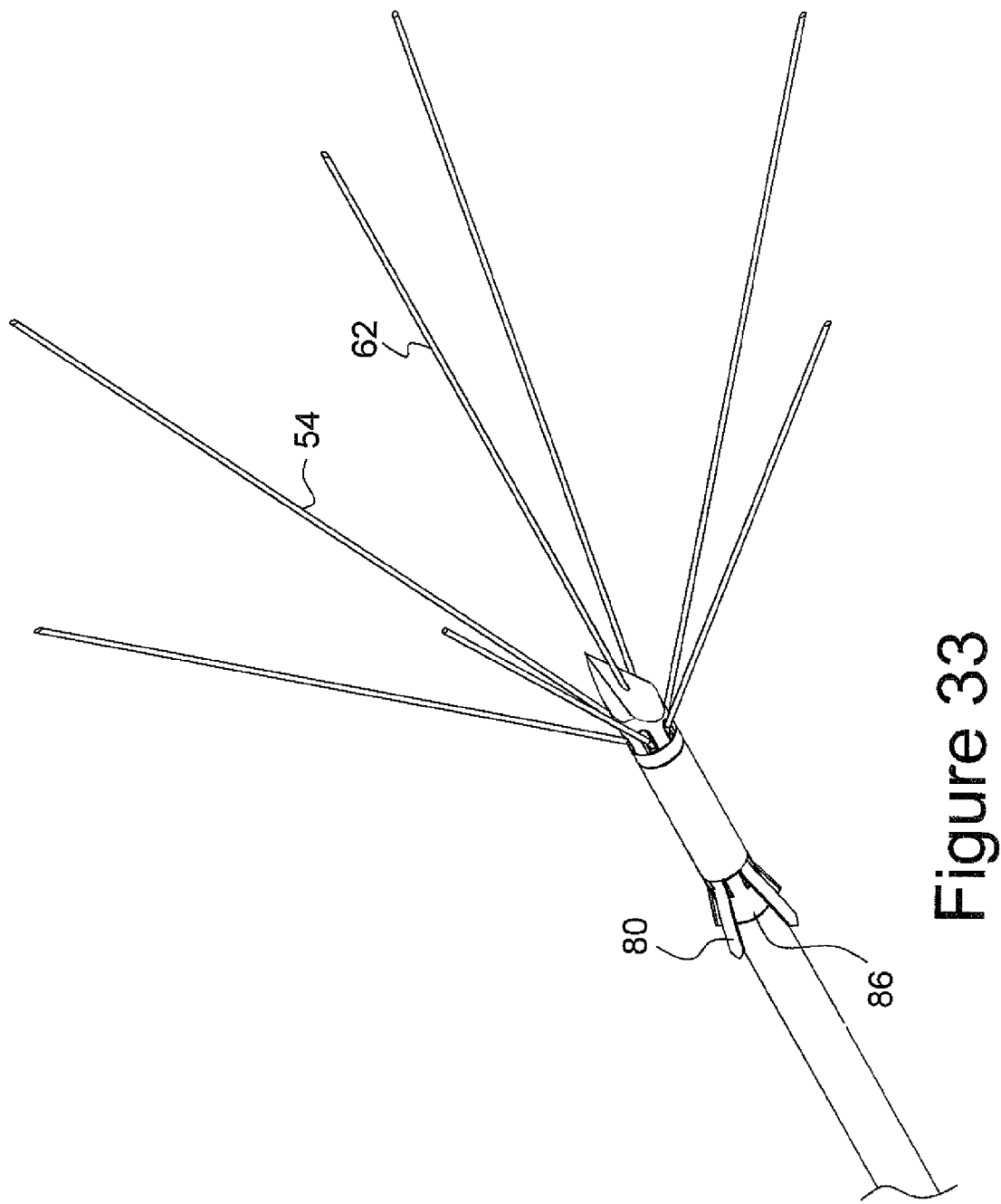
FIG. 33 is a detail perspective view illustrating deployment of anchors and hypotube ablation stylets.

Electrode mandrel tube 74 is secured at its proximal end to handle 14. At its distal end, electrode mandrel tube 74 is secured to trocar 32, for example by a quantity of epoxy adhesive 100 in the annular groove 102 on trocar 32, as illustrated in FIG. 3. Stylet actuator 16 is secured to electrode push tube 66. Thus, movement in the direction of arrow 68 in FIG. 1 causes the stylets to emerge from the end of the catheter as illustrated in FIGS. 5, 6, 7 and 32. Full deployment of ablation electrodes or stylets 54 and 62 is illustrated most clearly in FIG. 33.

Anchoring actuator 18 is secured to anchor push tube 78. At its distal end, electrode mandrel tube 74 is secured to anchor mandrel 86, for example by a quantity of epoxy adhesive. Accordingly, movement of anchoring actuator 18, in the direction of arrow 70 in FIG. 1, causes the anchors 80 to emerge from the catheter as illustrated in FIGS. 5, 6, 7 and 32. Full deployment of anchors 80 is illustrated most clearly in FIG. 33.

In accordance with the present invention it is contemplated that control of the inventive ablation device 10 will be achieved by one or two electrical switches 104 and 106. Operation of switch 106 will cause the appearance of a menu on a display, for example by axial movement of switch 106 in the manner of a joystick. Transverse movement of switch 106 causes the menu to switch between different menu items, such as controlling ablation time, controlling ablation temperature, or some other parameter. Selection of the desired value for the selected parameter is achieved by transverse motion of switch 106, causing the various values to be displayed on the display. When the desired value is seen on the screen by the surgeon, depression of switch 104 registers that value with the electronic circuit controlling ablation and causes the inventive ablation device 10 to be operated in accordance with the selected parameter.

RF ablation energy, control signals, and temperature measurement signals are coupled from the inventive ablation device 10 to a control unit/RF energy source by a connector 108. In accordance with the present invention, it is contemplated that a conventional radiofrequency energy source such as that used in conventional ablation systems would be employed in conjunction with the inventive ablation device 10.

In accordance with the present invention, cauterization radiofrequency energy may also be applied to trocar 32 during withdrawal of trocar 32 from the patient in order to control loss of blood. It is noted that the nature of the RF signal needed to achieve cautery is different from the nature of an ablation signal. Both of these signals are well defined in the art. Likewise, their generation is also well-known. However, in accordance of the present invention conventional cautery and conventional ablation signals may be used for cautery and ablation, respectively.

An alternative embodiment of the inventive catheter 112 is illustrated in FIG. 34. Here anchors 180 are positioned distally of ablation electrodes 154.

While the inventive device has been illustrated for use in the ablation of uterine fibroids, it is understood that this particular implementation is exemplary and that the inventive device may be employed in a wide variety of circumstances. Likewise, while an illustrative embodiment of the invention has been described, it is understood that various modifications to the structure of the disclosed device will be obvious to those of ordinary skill in the art. Such modifications are within the spirit and scope of the invention which is limited and defined only by the appended claims.

The invention claimed is:

1. An ablation element, comprising:
   (a) an elongated cannula having a proximal end and a distal end, said cannula defining an internal lumen within said cannula and a cannula axis;
   (b) a plurality of conductors contained within said lumen, each of said conductors having a proximal end proximate the proximal end of said cannula, and a distal end proximate the distal end of said cannula;
   (c) a plurality of ablation stylets each having a proximal end and a distal end, and each coupled at the respective proximal end of said stylet to the distal end of a respective conductor, said stylets comprising a deflectable material, said conductors together with their respective stylets being mounted for axial movement;
   (d) a trocar point defined proximate the distal end of said cannula;
   (e) a deflection surface positioned between said trocar point and said proximal end of said cannula, the deflection surface being configured and positioned to deflect, in response to axial movement of said stylets in a direction from said proximate end of said cannula to said distal end of said cannula, at least some of said stylets laterally with respect to said cannula axis in different directions along substantially straight paths, said paths defining an ablation volume; and
   (f) a central conductor contained within said lumen, said central conductor having a proximal end proximate the proximal end of said cannula, and a distal end proximate the distal end of said cannula; said central conductor coupled with at least one central ablation stylet having a proximal end and a distal end, and coupled at the respective proximal end of said central ablation stylet to the distal end of said central conductor, said central ablation stylet comprising a deflectable material, said central conductor together with said central ablation stylet being mounted for axial movement and in response to axial movement of said central ablation stylet in a direction from said proximate end of said cannula to said distal end of said cannula, said central ablation stylet extends along said cannula axis.

2. An ablation element as in claim 1, wherein said conductor is selected from the group consisting of electrical conductors, radio frequency conductors, microwave conductors and optical conductors.

3. An ablation element as in claim 1, wherein each of said conductors are integral with its respective ablation stylet.

4. An ablation element as in claim 1, wherein the solid contents of said lumen consist essentially of said conductors.

5. An ablation element as in claim 1, wherein each of said stylets are configured to assume a substantially straight configuration in the absence of external forces.

6. An ablation element as in claim 1, further comprising:
   (f) a motor member or members coupled to said conductors to drive axial movement of said stylets in directions from said proximal end of said cannula to said distal end of said cannula, and from said distal end of said cannula to said proximal end of said cannula through a plurality of positions.

7. An ablation element as in claim 1, wherein said trocar point is defined at the distal end of a trocar member, said trocar member having an outside surface, said cannula having an outside surface, said trocar member having a proximal end secured proximate to the distal end of said elongated cannula, and the outside surface of said cannula and the outside surface of said trocar point defining a trocar surface.

8. An ablation element as in claim 7, wherein said deflection surface comprises a number of ramps defined proximate the proximal end of said trocar point, the distal ends of said stylets being positionable proximate to said ramps and within said trocar surface.

9. An ablation element as in claim 8, wherein said conductors are electrical conductors, said stylets are electrical conductors, and each of said stylets are configured to assume a substantially straight configuration in the absence of external forces.

10. An ablation element as in claim 9, wherein said deflection surface comprises a plurality of channels guiding said distal ends of said stylets to said ramps.

11. An ablation element as in claim 9, wherein said cannula is secured to said trocar member with the outside surface of said cannula proximate to the outside surface of said trocar member.

12. An ablation element as in claim 1, further comprising:
   (f) an anchor mounted for movement between an internal position disposed within said trocar surface and an anchoring position extending laterally from said trocar surface through points external of said lumen; and (g) a drive member disposed within said lumen and coupled to said anchor to drive said anchor between said internal position and said anchoring position.

13. An ablation element as in claim 12, wherein said anchor comprises at least two pointed members mounted for movement in directions which have vector components which extend away from the axis or said cannula and away from each other.

14. An ablation element as in claim 13, wherein said pointed members extend in a direction with vector component that extends in a direction opposite to the direction in which said trocar point extends.

15. An ablation element as in claim 1, wherein said conductors bear against each other at least along a portion of their length within said cannula.

16. An ablation element, comprising:
   (a) an elongated cannula having a proximal end and a distal end, said cannula defining an internal lumen within said cannula and a cannula axis;
   (b) a plurality of conductors contained within said lumen, each of said conductors having a proximal end proximate the proximal end of said cannula, and a distal end proximate the distal end of said cannula;
   (c) a plurality of ablation stylets each having a proximal end and a distal end, and each coupled at the respective proximal end of said stylet to the distal end of a respective conductor, said stylets comprising a deflectable material, said conductors together with their respective stylets being mounted for axial movement;
   (d) a front end defined proximate the distal end of said cannula;
   (e) a deflection surface positioned between said front end and said proximal end of said cannula, the deflection surface being configured and positioned to deflect, in response to axial movement of said stylets in a direction from said proximate end of said cannula to said distal end of said cannula, at least some of said stylets laterally with respect to said cannula axis in different directions along substantially straight paths, said paths defining an ablation volume; and
   (f) a central conductor contained within said lumen, said central conductor having a proximal end proximate the proximal end of said cannula, and a distal end proximate the distal end of said cannula; said central conductor coupled with at least one central ablation stylet having a proximal end and a distal end, and coupled at the respective proximal end of said central ablation stylet to the distal end of said central conductor, said central ablation stylet comprising a deflectable material, said central conductor together with said central ablation stylet being mounted for axial movement and in response to axial movement of said central ablation stylet in a direction from said proximate end of said cannula to said distal end of said cannula, said central ablation stylet extends along said cannula axis.

17. An ablation element as in claim 16, wherein said conductors bear against each other at least along a portion of their length within said cannula.

18. An ablation element as in claim 16, wherein said conductors are driven by a drive mechanism which allows said conductors to move independently.

19. An ablation element as in claim 16, wherein said conductors have a length, a width and a thickness, said width being greater than said thickness.

20. An ablation element as in claim 16, wherein said conductors terminate in a point oriented to allow deflection by said deflection surface.

21. An ablation element as in claim 16, wherein said conductors extend in different directions when they exit the deflection surface and extend to a variable extent.

22. An ablation element as in claim 16, wherein said conductors are driven by a drive circuit which varies the amount of energy supplied to the stylets and/or the length of the stylets and/or the length of the stylets and/or the time during which power is supplied to the stylets and/or the angular orientation of the ablation element.

23. An ablation element as in claim 22, wherein the parameters of stylet length, stylet power, stylet actuation time and/or angular orientation are controlled by a computer in response to a computer program having an input comprising feedback information from the tissue area being operated on and/or a preset program.

24. An ablation element, comprising:
   (a) an elongated cannula having a proximal end and a distal end, said cannula defining an internal lumen within said cannula and a cannula axis;
   (b) a plurality of ablation stylets, each of ablation stylets having a proximal end and a distal end, said ablation stylets being joined to each other in the configuration where said distal ends of said ablat stylets are free to be deflected, said ablation stylets forming a unitary ablation stylet array, said unitary ablation stylet array being mounted for sliding movement with respect to said elongated cannula, and said ablation stylets comprising a deflectable material;
   (c) an ablation stylet sliding member, said ablation stylet sliding member having a proximal end proximate the proximal end of said cannula, and a distal end positionable proximate the distal end of said cannula, said ablation stylet sliding member being mounted for sliding movement with respect to said cannula, and said ablation stylet sliding member being an effective conductor of energy; and
   (d) a trocar point assembly defining a trocar point, said trocar point assembly being secured to said cannula proximate the distal end of said cannula, said trocar point assembly comprising:
      (i) a plurality of tracks for receiving and guiding sliding movement of said ablation stylets;
      (ii) a plurality of stylet deflection surfaces positioned between said trocar point and said proximal end of said cannula, the stylet deflection surfaces being configured and positioned to deflect, in response to axial movement of said stylets in a direction from said proximate end of said cannula to said distal end of said cannula, at least one of said stylets away from said cannula axis and in different directions along substantially straight paths, said straight paths defining an ablation volume;
   (e) an anchor, said anchor having a proximal end and a distal end, said anchor having an end free to be deflected, said anchor forming a unitary anchoring array, said unitary anchoring array being mounted for sliding movement with respect to said elongated cannula, and said anchor comprising a deflectable material; and
   (f) an anchor sliding member, said anchor sliding member being mounted for sliding movement with respect to said cannula, and said anchor sliding member being an effective conductor of energy; and wherein said trocar point assembly further comprises (iii) an anchor deflection surface positioned between said trocar point and said proximal end of said cannula, the anchor deflection surface being configured and positioned to deflect, in response to axial movement of said anchor, said anchor away from said cannula axis to act as a barb.

25. An ablation element as in claim 24, wherein a graphical user interface and a pair of electrical switches, such as a joystick and a pushbutton, will be used to switch between operating parameter options for the inventive catheter which are displayed on a graphical user interface or other information conveying device such as an audio cue generator, the surgeon navigates using said pair of electrical switches by looking at or hearing electronically generated audio signal, such as a voice, presenting various options and selects that option by pushing an electrical switch.

26. An ablation element as in claim 24, wherein electrical switches which operate the system may be recessed partially or fully in order to minimize the likelihood of unintentional actuation.

27. An ablation element as in claim 26, wherein a human voice present options and acknowledge instructions, allowing the surgeon to operate without having to look away from visual displays guiding the operation, the patient, instruments and so forth, thus removing potential losses of information.

28. An ablation element as in claim 24, wherein laser manufacturing techniques are used to manufacture the anchors.

29. An ablation element as in claim 24, wherein the point of the trocar is comprises three deflections surfaces, said stylets configured to cooperate with said deflection surfaces using a low friction insulator ring.

30. An ablation element as in claim 24, wherein rearwardly deployed anchoring stylets which act as retractable barbs for maintaining the position of the trocar point during forward deployment of the radiofrequency (RF) electrode ablation stylets.

31. An ablation element as in claim 24, wherein a stylet operating member is positioned on one side of a tubular compression/tension operator, and anchor member operating member, is positioned on the other side of said tubular compression/tension operator.

32. An ablation element as in claim 31, wherein the compression/tension operator is secured at the proximal end to the handle of the ablation instrument and at the distal and to the anchoring member deflection surface and the stylet deflection surface.

33. An ablation element as in claim 24, wherein a plurality of hypotube electrode stylets which are bound together as a unitary structure and advanced by a single push tube or wire.

34. An ablation element as in claim 24, wherein channels for flushing are provided and the frequency with which flushing should be performed is minimized through the use of a trocar font face which is substantially closed but allowing said stylets to exit through the cylindrical side wall of the trocar point.

35. An ablation element as in claim 24, wherein the anchor member is separate from the anchor push tube, and is connected it to by mating or other interlocking structure.

36. An ablation element as in claim 24, wherein deflection surfaces for both the stylets and anchors are selected to result in strains in the range of two to 8%, preferably about 4%, for example 3.5% to 4.5%, which represents a reasonable compromise between instrument longevity and a relatively large amount of deflection.

37. An ablation element as in claim 24, wherein an insulation sleeve is positioned between the anchors and the stylets in order to allow separate electrical actuation and ablation with either or both of the anchors and the stylets.

38. An ablation element as in claim 24, wherein the stylets contain thermocouples which are used to measure the temperature of ablated tissue, thus ensuring that the tissue will be raised to the correct temperature for a sufficient period of time to ablate tissue resulting in the creation of necrotic tissue which may be absorbed by the body.

39. An ablation element as in claim 24, wherein stylets are deployed forwardly or distally while anchors are deployed in a proximal direction or rearwardly, or the stylets may be deployed in a proximal direction or rearwardly, while anchors are deployed forwardly or distally.

* * * * *